US012605431B2

(12) United States Patent
Choi et al.

(10) Patent No.: US 12,605,431 B2
(45) Date of Patent: Apr. 21, 2026

(54) COMPOSITION FOR TREATING OR PREVENTING MYOPATHY, OBESITY OR DIABETES

(71) Applicant: NB SCIENCE CO., LTD., Gyeonggi-do (KR)

(72) Inventors: Bong Keun Choi, Gyeonggi-do (KR); Sung Kwon Lee, Gyeonggi-do (KR); Sang Hyup Lee, Gyeonggi-do (KR)

(73) Assignee: NB SCIENCE CO., LTD., Gyeonggi-do (KR)

( * ) Notice: Subject to any disclaimer, the term of this patent is extended or adjusted under 35 U.S.C. 154(b) by 414 days.

(21) Appl. No.: 18/267,252

(22) PCT Filed: Dec. 14, 2021

(86) PCT No.: PCT/KR2021/018986
§ 371 (c)(1),
(2) Date: Jun. 14, 2023

(87) PCT Pub. No.: WO2022/131756
PCT Pub. Date: Jun. 23, 2022

(65) Prior Publication Data
US 2024/0058428 A1 Feb. 22, 2024

(30) Foreign Application Priority Data

Dec. 14, 2020 (KR) ........................ 10-2020-0174841

(51) Int. Cl.
*A61K 38/48* (2006.01)
*A61P 21/00* (2006.01)
*C12N 9/64* (2006.01)

(52) U.S. Cl.
CPC .......... *A61K 38/4886* (2013.01); *A61P 21/00* (2018.01); *C12N 9/6489* (2013.01); *C12Y 304/24* (2013.01)

(58) Field of Classification Search
CPC ..... A61K 38/4886; C12N 9/6489; A61P 3/04; A61P 3/10; A61P 21/00
See application file for complete search history.

(56) References Cited

U.S. PATENT DOCUMENTS

| | | | |
|---|---|---|---|
| 9,950,043 B2 | 4/2018 | Feldman | |
| 2001/0049106 A1 | 12/2001 | Buckbinder et al. | |
| 2003/0032168 A1 | 2/2003 | Hirose et al. | |
| 2018/0140684 A1 | 5/2018 | Feldman | |

FOREIGN PATENT DOCUMENTS

| | | |
|---|---|---|
| KR | 10-2010-0135779 A | 12/2010 |
| WO | WO-2007/147497 A2 | 12/2007 |

OTHER PUBLICATIONS

International Search Report from corresponding PCT Application No. PCT/KR2021/018986, dated Apr. 8, 2022.
NCBI, GenBank Accession No. NP_008919.3. A disintegrin and metalloproteinase with thrombospondin motifs 1 preproprotein [*Homo sapiens*], Nov. 18, 2020.
Peters, B. J. M. et al. "Variants of ADAMTS1 modify the effectiveness of statins in reducing the risk of myocardial infarction", Pharmacogenetics and genomics, 2010, vol. 20, pp. 766-774.
Office Action from corresponding Korean Patent Application No. 10-2020-0174841, dated May 24, 2022.
Notice of Allowance from corresponding Korean Patent Application No. 10-2020-0174841. dated Oct. 17, 2022.
Extended European Search Report from corresponding European Patent Application No. 21907060.4, dated Jul. 10, 2024.

*Primary Examiner* — Ruth A Davis
(74) *Attorney, Agent, or Firm* — Harness, Dickey & Pierce, P.L.C.

(57) ABSTRACT

The present invention relates to: an M3 mutant peptide; a composition for alleviating, inhibiting, preventing or treating myopathy, obesity or diabetes, comprising same as an active ingredient; a method for alleviating, inhibiting, preventing or treating myopathy, obesity or diabetes by using the M3 mutant peptide; and uses of the M3 mutant peptide for alleviating, inhibiting, preventing or treating myopathy, obesity or diabetes.

5 Claims, 23 Drawing Sheets
Specification includes a Sequence Listing.

WB: 6x-His

Control

WT

M3 Mutant

Control

WT

M3 Mutant

M4 Mutant

M5 Mutant

M6 Mutant

†<0.01, ‡<0.001 (compared to Normal group)

*<0.05, <0.01, *<0.001 (compared to Dexa group)

Normal        Induced muscle loss        Treated with M3

SEQUENCE LISTING

<160> NUMBER OF SEQ ID NOS: 4

<210> SEQ ID NO 1
<211> LENGTH: 967
<212> TYPE: PRT
<213> ORGANISM: Artificial Sequence
<220> FEATURE:

<223> OTHER INFORMATION: ADAMTS1

<400> SEQUENCE: 1

Met Gln Arg Ala Val Pro Glu Gly Phe Gly Arg Arg Lys Leu Gly Ser
1               5                   10                  15

Asp Met Gly Asn Ala Glu Arg Ala Pro Gly Ser Arg Ser Phe Gly Pro
                20                  25                  30

Val Pro Thr Leu Leu Leu Leu Ala Ala Ala Leu Leu Ala Val Ser Asp
            35                  40                  45

Ala Leu Gly Arg Pro Ser Glu Glu Asp Glu Glu Leu Val Val Pro Glu
        50                  55                  60

Leu Glu Arg Ala Pro Gly His Gly Thr Thr Arg Leu Arg Leu His Ala
65                  70                  75                  80

Phe Asp Gln Gln Leu Asp Leu Glu Leu Arg Pro Asp Ser Ser Phe Leu
                85                  90                  95

Ala Pro Gly Phe Thr Leu Gln Asn Val Gly Arg Lys Ser Gly Ser Glu
                100                 105                 110

Thr Pro Leu Pro Glu Thr Asp Leu Ala His Cys Phe Tyr Ser Gly Thr
            115                 120                 125

Val Asn Gly Asp Pro Ser Ser Ala Ala Ala Leu Ser Leu Cys Glu Gly
        130                 135                 140

Val Arg Gly Ala Phe Tyr Leu Leu Gly Glu Ala Tyr Phe Ile Gln Pro
145                 150                 155                 160

Leu Pro Ala Ala Ser Glu Arg Leu Ala Thr Ala Ala Pro Gly Glu Lys
                165                 170                 175

Pro Pro Ala Pro Leu Gln Phe His Leu Leu Arg Arg Asn Arg Gln Gly
                180                 185                 190

Asp Val Gly Gly Thr Cys Gly Val Val Asp Asp Glu Pro Arg Pro Thr
            195                 200                 205

Gly Lys Ala Glu Thr Glu Asp Glu Asp Glu Gly Thr Glu Gly Glu Asp
        210                 215                 220

Glu Gly Ala Gln Trp Ser Pro Gln Asp Pro Ala Leu Gln Gly Val Gly
225                 230                 235                 240

Gln Pro Thr Gly Thr Gly Ser Ile Arg Lys Lys Arg Phe Val Ser Ser
                245                 250                 255

His Arg Tyr Val Glu Thr Met Leu Val Ala Asp Gln Ser Met Ala Glu
                260                 265                 270

Phe His Gly Ser Gly Leu Lys His Tyr Leu Leu Thr Leu Phe Ser Val
            275                 280                 285

Ala Ala Arg Leu Tyr Lys His Pro Ser Ile Arg Asn Ser Val Ser Leu
        290                 295                 300

Val Val Val Lys Ile Leu Val Ile His Asp Glu Gln Lys Gly Pro Glu
305                 310                 315                 320

Val Thr Ser Asn Ala Ala Leu Thr Leu Arg Asn Phe Cys Asn Trp Gln
                325                 330                 335

Lys Gln His Asn Pro Pro Ser Asp Arg Asp Ala Glu His Tyr Asp Thr
            340                 345                 350

Ala Ile Leu Phe Thr Arg Gln Asp Leu Cys Gly Ser Gln Thr Cys Asp
            355                 360                 365

Thr Leu Gly Met Ala Asp Val Gly Thr Val Cys Asp Pro Ser Arg Ser
        370                 375                 380

Cys Ser Val Ile Glu Asp Asp Gly Leu Gln Ala Ala Phe Thr Thr Ala
385                 390                 395                 400

```
His Glu Leu Gly His Val Phe Asn Met Pro His Asp Asp Ala Lys Gln
                405             410             415

Cys Ala Ser Leu Asn Gly Val Asn Gln Asp Ser His Met Met Ala Ser
            420             425             430

Met Leu Ser Asn Leu Asp His Ser Gln Pro Trp Ser Pro Cys Ser Ala
            435             440             445

Tyr Met Ile Thr Ser Phe Leu Asp Asn Gly His Gly Glu Cys Leu Met
    450             455             460

Asp Lys Pro Gln Asn Pro Ile Gln Leu Pro Gly Asp Leu Pro Gly Thr
465             470             475             480

Ser Tyr Asp Ala Asn Arg Gln Cys Gln Phe Thr Phe Gly Glu Asp Ser
            485             490             495

Lys His Cys Pro Asp Ala Ala Ser Thr Cys Ser Thr Leu Trp Cys Thr
            500             505             510

Gly Thr Ser Gly Gly Val Leu Val Cys Gln Thr Lys His Phe Pro Trp
            515             520             525

Ala Asp Gly Thr Ser Cys Gly Glu Gly Lys Trp Cys Ile Asn Gly Lys
    530             535             540

Cys Val Asn Lys Thr Asp Arg Lys His Phe Asp Thr Pro Phe His Gly
545             550             555             560

Ser Trp Gly Met Trp Gly Pro Trp Gly Asp Cys Ser Arg Thr Cys Gly
            565             570             575

Gly Gly Val Gln Tyr Thr Met Arg Glu Cys Asp Asn Pro Val Pro Lys
            580             585             590

Asn Gly Gly Lys Tyr Cys Glu Gly Lys Arg Val Arg Tyr Arg Ser Cys
            595             600             605

Asn Leu Glu Asp Cys Pro Asp Asn Asn Gly Lys Thr Phe Arg Glu Glu
    610             615             620

Gln Cys Glu Ala His Asn Glu Phe Ser Lys Ala Ser Phe Gly Ser Gly
625             630             635             640

Pro Ala Val Glu Trp Ile Pro Lys Tyr Ala Gly Val Ser Pro Lys Asp
            645             650             655

Arg Cys Lys Leu Ile Cys Gln Ala Lys Gly Ile Gly Tyr Phe Phe Val
            660             665             670

Leu Gln Pro Lys Val Val Asp Gly Thr Pro Cys Ser Pro Asp Ser Thr
            675             680             685

Ser Val Cys Val Gln Gly Gln Cys Val Lys Ala Gly Cys Asp Arg Ile
    690             695             700

Ile Asp Ser Lys Lys Lys Phe Asp Lys Cys Gly Val Cys Gly Gly Asn
705             710             715             720

Gly Ser Thr Cys Lys Lys Ile Ser Gly Ser Val Thr Ser Ala Lys Pro
            725             730             735

Gly Tyr His Asp Ile Ile Thr Ile Pro Thr Gly Ala Thr Asn Ile Glu
            740             745             750

Val Lys Gln Arg Asn Gln Arg Gly Ser Arg Asn Asn Gly Ser Phe Leu
            755             760             765

Ala Ile Lys Ala Ala Asp Gly Thr Tyr Ile Leu Asn Gly Asp Tyr Thr
    770             775             780

Leu Ser Thr Leu Glu Gln Asp Ile Met Tyr Lys Gly Val Val Leu Arg
785             790             795             800

Tyr Ser Gly Ser Ser Ala Ala Leu Glu Arg Ile Arg Ser Phe Ser Pro
            805             810             815

Leu Lys Glu Pro Leu Thr Ile Gln Val Leu Thr Val Gly Asn Ala Leu
```

```
            820                 825                 830

Arg Pro Lys Ile Lys Tyr Thr Tyr Phe Val Lys Lys Lys Lys Glu Ser
        835                 840                 845

Phe Asn Ala Ile Pro Thr Phe Ser Ala Trp Val Ile Glu Glu Trp Gly
    850                 855                 860

Glu Cys Ser Lys Ser Cys Glu Leu Gly Trp Gln Arg Arg Leu Val Glu
865                 870                 875                 880

Cys Arg Asp Ile Asn Gly Gln Pro Ala Ser Glu Cys Ala Lys Glu Val
                885                 890                 895

Lys Pro Ala Ser Thr Arg Pro Cys Ala Asp His Pro Cys Pro Gln Trp
                900                 905                 910

Gln Leu Gly Glu Trp Ser Ser Cys Ser Lys Thr Cys Gly Lys Gly Tyr
            915                 920                 925

Lys Lys Arg Ser Leu Lys Cys Leu Ser His Asp Gly Gly Val Leu Ser
        930                 935                 940

His Glu Ser Cys Asp Pro Leu Lys Lys Pro Lys His Phe Ile Asp Phe
945                 950                 955                 960

Cys Thr Met Ala Glu Cys Ser
                965

<210> SEQ ID NO 2
<211> LENGTH: 382
<212> TYPE: PRT
<213> ORGANISM: Artificial Sequence
<220> FEATURE:
<223> OTHER INFORMATION: M3

<400> SEQUENCE: 2

Met Gln Arg Ala Val Pro Glu Gly Phe Gly Arg Arg Lys Leu Gly Ser
1               5                   10                  15

Asp Met Gly Asn Ala Glu Arg Ala Pro Gly Ser Arg Ser Phe Gly Pro
                20                  25                  30

Val Pro Thr Leu Leu Leu Leu Ala Ala Ala Leu Leu Ala Val Ser Asp
            35                  40                  45

Ala Leu Gly Arg Pro Ser Glu Glu Asp Glu Glu Leu Val Val Pro Glu
    50                  55                  60

Leu Glu Arg Ala Pro Gly His Gly Thr Thr Arg Leu Arg Leu His Ala
65                  70                  75                  80

Phe Asp Gln Gln Leu Asp Leu Glu Leu Arg Pro Asp Ser Ser Phe Leu
                85                  90                  95

Ala Pro Gly Phe Thr Leu Gln Asn Val Gly Arg Lys Ser Gly Ser Glu
            100                 105                 110

Thr Pro Leu Pro Glu Thr Asp Leu Ala His Cys Phe Tyr Ser Gly Thr
        115                 120                 125

Val Asn Gly Asp Pro Ser Ser Ala Ala Ala Leu Ser Leu Cys Glu Gly
    130                 135                 140

Val Arg Gly Ala Phe Tyr Leu Leu Gly Glu Ala Tyr Phe Ile Gln Pro
145                 150                 155                 160

Leu Pro Ala Ala Ser Glu Arg Leu Ala Thr Ala Ala Pro Gly Glu Lys
                165                 170                 175

Pro Pro Ala Pro Leu Gln Phe His Leu Leu Arg Arg Asn Arg Gln Gly
            180                 185                 190

Asp Val Gly Gly Thr Cys Gly Val Val Asp Asp Glu Pro Arg Pro Thr
        195                 200                 205

Gly Lys Ala Glu Thr Glu Asp Glu Asp Glu Gly Thr Glu Arg Phe Val
```

-continued

```
      210              215              220

Ser Ser His Arg Tyr Val Glu Thr Met Leu Val Ala Asp Gln Ser Met
225              230              235              240

Ala Glu Phe His Gly Ser Gly Leu Lys His Tyr Leu Leu Thr Leu Phe
             245              250              255

Ser Val Ala Ala Arg Leu Tyr Lys His Pro Ser Ile Arg Asn Ser Val
             260              265              270

Ser Leu Val Val Val Lys Ile Leu Val Ile His Asp Glu Gln Lys Gly
         275              280              285

Pro Glu Val Thr Ser Asn Ala Ala Leu Thr Leu Arg Asn Phe Cys Asn
     290              295              300

Trp Gln Lys Gln His Asn Pro Pro Ser Asp Arg Asp Ala Glu His Tyr
305              310              315              320

Asp Thr Ala Ile Leu Phe Thr Arg Gln Asp Leu Cys Gly Ser Gln Thr
             325              330              335

Cys Asp Thr Leu Gly Met Ala Asp Val Gly Thr Val Cys Asp Pro Ser
             340              345              350

Arg Ser Cys Ser Val Ile Glu Asp Asp Gly Leu Gln Ala Ala Phe Thr
         355              360              365

Thr Ala His Glu Leu Gly His Val Phe Asn Met Pro His Asp
     370              375              380
```

```
<210> SEQ ID NO 3
<211> LENGTH: 2904
<212> TYPE: DNA
<213> ORGANISM: Artificial Sequence
<220> FEATURE:
<223> OTHER INFORMATION: ADAMTS1

<400> SEQUENCE: 3
atgcagcgag ctgtgcccga ggggttcgga aggcgcaagc tgggcagcga catggggaac      60
gcggagcggg ctccggggtc tcggagcttt gggccagtac ccacgctgct gctgctcgcc     120
gcggcgctac tggccgtgtc ggacgcactc gggcgcccct ccgaggagga cgaggagcta     180
gtggtgccgg agctggagcg cgccccggga cacgggacca cgcgcctccg cctgcacgcc     240
tttgaccagc agctggatct ggagctgcgg cccgacagca gcttttttggc gcccggcttc     300 acgctccaga acgtggggcg caaatccggg tccgagacgc cgcttccgga aaccgacctg     360
gcgcactgct tctactccgg caccgtgaat ggcgatccca gctcggctgc cgccctcagc     420
ctctgcgagg gcgtgcgcgg cgccttctac ctgctggggg aggcgtattt catccagccg     480
ctgcccgccg ccagcgagcg cctcgccacc gccgccccag gggagaagcc gccggcacca     540
ctacagttcc acctcctgcg gcggaatcgg cagggcgacg tcggcggcac gtgcggggtc     600
gtggacgacg agccccggcc gactgggaaa gcggagaccg aagacgagga cgaagggact     660
gagggcgagg acgaaggggc tcagtggtcg ccgcaggacc cggcactgca aggcgtagga     720
cagcccacag gaactggaag cataagaaag aagcgatttg tgtccagtca ccgctatgtg     780
gaaaccatgc ttgtggcaga ccagtcgatg gcagaattcc acggcagtgg tctaaagcat     840
taccttctca cgttgttttc ggtggcagcc agattgtaca acacccccag cattcgtaat     900
tcagttagcc tggtggtggt gaagatcttg gtcatccacg atgaacagaa ggggccggaa     960
gtgacctcca atgctgccct cactctgcgg aactttttgca actggcagaa gcagcacaac    1020
ccacccagtg accgggatgc agagcactat gacacagcaa ttcttttcac cagacaggac    1080
ttgtgtgggt cccagacatg tgatactctt gggatggctg atgttggaac tgtgtgtgat    1140
```

-continued

```
ccgagcagaa gctgctccgt catagaagat gatggtttac aagctgcctt caccacagcc      1200
catgaattag gccacgtgtt taacatgcca catgatgatg caaagcagtg tgccagcctt      1260
aatggtgtga accaggattc ccacatgatg gcgtcaatgc tttccaacct ggaccacagc      1320
cagccttggt ctccttgcag tgcctacatg attacatcat ttctggataa tggtcatggg      1380
gaatgtttga tggacaagcc tcagaatccc atacagctcc caggcgatct ccctggcacc      1440
tcgtacgatg ccaaccggca gtgccagttt acatttgggg aggactccaa acactgcccc      1500
gatgcagcca gcacatgtag caccttgtgg tgtaccggca cctctggtgg ggtgctggtg      1560
tgtcaaacca aacacttccc gtgggcggat ggcaccagct gtggagaagg gaaatggtgt      1620
atcaacggca agtgtgtgaa caaaaccgac agaaagcatt ttgatacgcc ttttcatgga      1680
agctggggaa tgtggggggcc ttggggagac tgttcgagaa cgtgcggtgg aggagtccag      1740
tacacgatga gggaatgtga caacccagtc ccaaagaatg gagggaagta ctgtgaaggc      1800
aaacgagtgc gctacagatc ctgtaacctt gaggactgtc cagacaataa tggaaaaacc      1860
tttagagagg aacaatgtga agcacacaac gagtttttcaa aagcttcctt tgggagtggg      1920
cctgcggtgg aatggattcc caagtacgct ggcgtctcac caaggacag tgcaagctc        1980 atctgccaag ccaaaggcat tggctacttc ttcgtttttgc agcccaaggt tgtagatggt      2040
actccatgta gcccagattc cacctctgtc tgtgtgcaag gacagtgtgt aaaagctggt      2100
tgtgatcgca tcatagactc caaaaagaag tttgataaat gtggtgtttg cggggggaaat      2160 ggatctactt gtaaaaaaat atcaggatca gttactagtg caaaacctgg atatcatgat      2220
atcatcacaa ttccaactgg agccaccaac atcgaagtga aacagcggaa ccagagggga      2280
tccaggaaca atggcagctt tcttgccatc aaagctgctg atggcacata tattcttaat      2340
ggtgactaca ctttgtccac cttagagcaa gacattatgt acaaaggtgt tgtcttgagg      2400
tacagcggct cctctgcggc attggaaaga attcgcagct ttagccctct caaagagccc      2460
ttgaccatcc aggttcttac tgtgggcaat gcccttcgac ctaaaattaa atacacctac      2520
ttcgtaaaga agaagaagga atctttcaat gctatcccca cttttttcagc atgggtcatt      2580 gaagagtggg gcgaatgttc taagtcatgt gaattgggtt ggcagagaag actggtagaa      2640
tgccgagaca ttaatggaca gcctgcttcc gagtgtgcaa aggaagtgaa gccagccagc      2700
accagacctt gtgcagacca tccctgcccc cagtggcagc tggggggagtg gtcatcatgt      2760 tctaagacct gtgggaaggg ttacaaaaaa agaagcttga agtgtctgtc ccatgatgga      2820
ggggtgttat ctcatgagag ctgtgatcct ttaaagaaac ctaaacattt catagacttt      2880
tgcacaatgg cagaatgcag ttaa                                            2904
```

```
<210> SEQ ID NO 4
<211> LENGTH: 1146
<212> TYPE: DNA
<213> ORGANISM: Artificial Sequence
<220> FEATURE:
<223> OTHER INFORMATION: M3

<400> SEQUENCE: 4
atgcagcgag ctgtgcccga gggggttcgga aggcgcaagc tgggcagcga catggggaac       60
gcggagcggg ctccgggggtc tcggagcttt gggccagtac ccacgctgct gctgctcgcc      120
gcggcgctac tggccgtgtc ggacgcactc gggcgcccct ccgaggagga cgaggagcta       180
gtggtgccgg agctggagcg cgccccggga cacgggacca cgcgcctccg cctgcacgcc       240
```

-continued

```
tttgaccagc agctggatct ggagctgcgg cccgacagca gcttttttggc gcccggcttc    300 acgctccaga acgtggggcg caaatccggg tccgagacgc cgcttccgga aaccgacctg    360
gcgcactgct tctactccgg caccgtgaat ggcgatccca gctcggctgc cgccctcagc    420
ctctgcgagg gcgtgcgcgg cgccttctac ctgctggggg aggcgtattt catccagccg    480
ctgcccgccg ccagcgagcg cctcgccacc gccgcccccag gggagaagcc gccggcacca    540
ctacagttcc acctcctgcg gcggaatcgg cagggcgacg tcggcggcac gtgcgggggtc    600 gtggacgacg agccccggcc gactgggaaa gcggagaccg aagacgagga cgaagggact    660
gagcgatttg tgtccagtca ccgctatgtg gaaaccatgc ttgtggcaga ccagtcgatg    720
gcagaattcc acggcagtgg tctaaagcat taccttctca cgttgttttc ggtggcagcc    780
agattgtaca aacaccccag cattcgtaat tcagttagcc tggtggtggt gaagatcttg    840
gtcatccacg atgaacagaa ggggccggaa gtgacctcca atgctgccct cactctgcgg    900
aacttttgca actggcagaa gcagcacaac ccacccagtg accgggatgc agagcactat    960
gacacagcaa ttcttttcac cagacaggac ttgtgtgggt cccagacatg tgatactctt   1020
gggatggctg atgttggaac tgtgtgtgat ccgagcagaa gctgctccgt catagaagat   1080
gatggtttac aagctgcctt caccacagcc catgaattag gccacgtgtt taacatgcca   1140
catgat                                                                 1146
```

COMPOSITION FOR TREATING OR PREVENTING MYOPATHY, OBESITY OR DIABETES

CROSS-REFERENCE TO RELATED APPLICATIONS

This application is a national phase application of PCT Application No. PCT/KR2021/018986, filed on 14 Dec. 2021, which claims the benefit and priority to Korean Patent Application No. 10-2020-0174841, filed on 14 Dec. 2020. The entire disclosures of the applications identified in this paragraph are incorporated herein by references.

TECHNICAL FIELD

The present disclosure relates to an M3 mutant peptide, a composition comprising the same as an active ingredient for alleviation, suppression, prevention, or treatment of a muscle disease, obesity, or diabetes, a method for alleviating, suppressing, preventing, or treating a muscle disease, obesity, or diabetes by using an M3 mutant peptide, and use of an M3 mutant peptide for alleviating, suppressing, preventing, or treating a muscle disease, obesity, or diabetes.

BACKGROUND

A reduction in human physical activity is a result of lifestyle changes due to the industrialization in modern society, and it has been a long time since the issue of negative effects on physical and mental health has been raised. Lack of exercise caused by reduced physical activity is a major cause of various lifestyle diseases including obesity and metabolic syndrome and causes a decrease in muscle mass. The muscle mass in the body plays a very important role in survival, and a decrease in skeletal muscle volume leads to a decrease in basal metabolic rate, a decrease in muscle strength, and the like, thereby making it difficult to maintain daily physical activity.

Muscle atrophy refers to a decrease in muscle volume, and symptoms thereof can be clearly evidently seen in patients suffering from cancer or various immunodeficiency diseases and are more prominent in patients with extremely restricted physical activity due to long-term bed life, physical handicapped person with restricted movement, and the elderly. The progression of aging causes sarcopenia indicating a decrease in muscle strength due to a continuous decrease in muscle volume, causing dangerous results that the elderly may be exposed to various life accidents.

With advancing years, both men and women undergo a change in body composition, and such a change occurs independently of the body weight change. In general, the change in body composition is considered to be due to a change in energy balance due to a weight gain, and the change in body composition appearing herein results in an increase in body fat but a decrease in muscle mass. The decrease in muscle mass gradually progresses from about 30 years of age, and sarcopenia in the elderly seriously affects functional disability, quality of life, and medical costs.

An increase in fat mass together with a decrease in muscle mass is referred to as sarcopenic obesity. A synergistic effect of an increase in body fat and a muscle atrophy will further increase the risk of functional disorders and metabolic disorders in the body.

Body mass index (BMI) and waist to hip ratio (WHR), which are used as indicators of obesity due to ease of access thereto in clinical practice, have limitations in that they do not reflect well the effects of age or exercise, changes in body composition due to weight loss, and the like. In particular, the muscle mass in the body composition has been reported to be related to metabolic syndrome and is suggested as a factor predicting the cause of all mortality. In recent years, in terms of health, there is an increasing need to pay attention to an increase in body fat percentage and a loss of muscle mass as factors related to insulin resistance, glucose metabolism, lipid concentration, and blood pressure.

Throughout the entire specification, many papers and patent documents are referenced and their citations are represented. The disclosures of cited papers and patent documents are entirely incorporated by reference into the present specification, and the level of the technical field within which the present disclosure falls and details of the present disclosure are explained more clearly.

DISCLOSURE OF INVENTION

Technical Problem

Therefore, in order to develop an agent for alleviation, suppression, prevention, or treatment of a muscle disease related to muscle loss, the present inventors screened for peptides having possibility of showing an effect against muscle loss, found that among the screened peptides, an M3 mutant peptide had significant muscle loss inhibitory activity, isolated and identified proteins having activity, and confirmed that the identified mutant peptides had superior activity compared with currently used medicines for muscle diseases related to muscle loss, and thereafter completed the present disclosure.

Accordingly, an aspect of the present disclosure is to provide an M3 mutant peptide.

Another aspect of the present disclosure is to provide a pharmaceutical composition comprising an M3 mutant peptide as an active ingredient for alleviation, suppression, prevention, or treatment of a muscle disease.

Still another aspect of the present disclosure is to provide a method for alleviating, suppressing, preventing, or treating muscle loss, the method including administering to a subject in need thereof an M3 mutant peptide in an amount effective to alleviate, suppress, prevent, or treat a muscle disease.

Still another aspect of the present disclosure is to provide use of an M3 mutant peptide for alleviation, suppression, prevention, or treatment of a muscle disease.

Aspect of the present disclosure is to provide a pharmaceutical composition comprising an M3 mutant peptide as an active ingredient for alleviation, suppression, prevention, or treatment of obesity.

Another aspect of the present disclosure is to provide a method for alleviating, suppressing, preventing, or treating obesity, the method including administering to a subject in need thereof an M3 mutant peptide in an amount effective to alleviate, suppress, prevent, or treat obesity.

Still another aspect of the present disclosure is to provide use of an M3 mutant peptide for alleviation, suppression, prevention, or treatment of obesity Aspect of the present disclosure is to provide a pharmaceutical composition comprising an M3 mutant peptide as an active ingredient for alleviation, suppression, prevention, or treatment of diabetes.

Another aspect of the present disclosure is to provide a method for alleviating, suppressing, preventing, or treating diabetes, the method including administering to a subject in need thereof an M3 mutant peptide in an amount effective to alleviate, suppress, prevent, or treat diabetes.

Still another aspect of the present disclosure is to provide use of an M3 mutant peptide for alleviation, suppression, prevention, or treatment of diabetes.

Other purposes and advantages of the present disclosure will become more obvious when taken with the following detailed description of the invention, claims, and drawings.

Solution to Problem

The present disclosure relates to an M3 mutant peptide, a composition comprising the same as an active ingredient for alleviation, suppression, prevention, or treatment of a muscle disease, obesity, or diabetes, and a method for alleviating, suppressing, preventing, or treating a muscle disease, obesity, or diabetes, by using an M3 mutant peptide.

Hereinafter, the present disclosure will be described in more detail.

In accordance with an aspect of the present disclosure, there is provided an M3 mutant peptide.

The M3 mutant peptide of the present disclosure is a mutant peptide of a wild-type of a disintegrin and metalloproteinase with thrombospondin motifs 1 (ADAMTS1).

ADAMTS1 is an enzyme that belongs to a disintegrin and metalloproteinase with thrombospondin motifs (ADAMTS), a family of multidomain extracellular protease, and is first found among 19 species of ADAMTS family enzymes discovered in humans. ADAMTS1 is known to inhibit angiogenesis by interaction with vascular endothelial growth factor A.

In the present disclosure, the M3 mutant peptide may be a peptide in which a portion of a peptide consisting of the amino acid sequence of SEQ ID NO: 1 is deleted.

In one specific embodiment of the present disclosure, the M3 mutant peptide of the present disclosure may include a deletion of at least one amino acid selected from the group consisting of amino acids at positions 223 to 261 of the peptide consisting of the amino acid sequence of SEQ ID NO: 1.

In one specific embodiment of the present disclosure, the M3 mutant peptide of the present disclosure may include a deletion of at least one position selected from the group consisting of arginine at position 249, lysine at position 250, lysine at position 251, and arginine at position 252 of the peptide consisting of the amino acid sequence of SEQ ID NO: 1, and for example, may include deletions of positions 249 to 251.

In one specific embodiment of the present disclosure, the M3 mutant peptide of the present disclosure may include a deletion of at least one position selected from the group consisting of arginine at position 249, lysine at position 250, lysine at position 251, and arginine at position 252 and a deletion of at least one amino acid selected from the group consisting of amino acids at positions 223 to 248 and 253 to 261 of the peptide consisting of the amino acid sequence of SEQ ID NO: 1. For example, the M3 mutant peptide of the present disclosure may include a deletion of at least one position selected from the group consisting of arginine at position 249, lysine at position 250, lysine at position 251, and arginine at position 252 and a deletion of at least one amino acid selected from the group consisting of amino acids at positions 223 to 248 of the peptide consisting of the amino acid sequence of SEQ ID NO: 1.

In the present disclosure, the deletion of at least one amino acid selected from the group consisting of the amino acids at positions 223 to 248 may be a deletion of an amino acid at position 223, or deletions of amino acids at positions 223 to 224, 223 to 225, 223 to 226, 223 to 227, 223 to 228, 223 to 229, 223 to 230, 223 to 231, 223 to 232, 223 to 233, 223 to 234, 223 to 235, 223 to 236, 223 to 237, 223 to 238, 223 to 239, 223 to 240, 223 to 241, 223 to 242, 223 to 243, 223 to 244, 223 to 245, 223 to 246, 223 to 247, or 223 to 248.

In the present disclosure, the deletion of at least one amino acid selected from the group consisting of amino acids at positions 253 to 261 may be a deletion of amino acid at position 253, or deletions of amino acids at positions 253 to 254, 253 to 255, 253 to 256, 253 to 257, 253 to 258, 253 to 259, 253 to 260, or 253 to 261.

In one specific embodiment of the present disclosure, the M3 mutant peptide of the present disclosure may further include deletions of aspartic acid at position 413 and serine at position 967 of the peptide consisting of the amino acid sequence of SEQ ID NO: 1.

In one specific embodiment of the present disclosure, the M3 mutant peptide of the present disclosure may include deletions of positions 223 to 251 and deletions of positions 413 to 967 of the peptide consisting of the amino acid sequence of SEQ ID NO: 1, and for example, may be a peptide consisting of the amino acid sequence of SEQ ID NO: 2.

In accordance with another aspect of the present disclosure, there is provided a pharmaceutical composition comprising the M3 mutant peptide of the present disclosure as an active ingredient for alleviation, suppression, prevention, or treatment of a muscle disease.

In the present disclosure, the M3 mutant peptide is as described above.

The distribution of body mass in muscle and adipose tissues has a significant influence on individual health. The balance between adipocyte differentiation and myocyte differentiation is known to involve many factors. For example, glucocorticoids, such as cortisol, natural hormones, or many synthetic cortisol analogues (including, e.g., prednisone, hydrocortisone, and dexamethasone), act on the body through the glucocorticoid receptor (GR). Glucocorticoids play an important role in regulating differentiation determination both in vivo and ex vivo, and promote adipogenesis and inhibit myogenesis. Androgen administration has been shown to influence the body composition to increase muscle mass while reducing fat mass.

Muscle insufficiency or weakness is one of the most devastating childhood health problems. These muscle disorders affect more than 1 in 3000 patients with various congenital myopathy and muscular dystrophy, such as Duchenne Muscular Dystrophy (DMD). These disorders are typically associated with genetic or spontaneous gene mutations. Children with these disorders suffer from a wide range of complications. Currently, the lack of effective therapy results in a high mortality rate, and new treatment strategies for such muscle diseases are needed.

The muscle tissue of adult vertebrates is regenerated from stem cells known as satellite cells or muscle stem cells (MuSCs). Satellite cells are distributed throughout muscle tissue, mitotically quiescent in the absence of injury or disease, and located in anatomically defined niches. In addition to the satellite cells, the type of cells that can contribute to muscle regeneration includes mesenchymal stem cells, bone marrow derived cells, muscle stromal cells, and mesenchymal stem cells, but are not limited thereto.

Tissue engineering involves the restoration or replacement of damaged or diseased tissues by a transplantation of a combination of cells, biomaterial scaffolds, biological active molecules, and genes. The basic premise of this approach is that exogenously introduced cells will improve the rate and extent of tissue repair.

Adult MuSCs can be transplanted into damaged or defective skeletal muscles to reconstruct muscle fibers and enhance functions, thereby potentially providing therapeutic applications of MuSCs. However, major obstacles in translating this technology are that there is a lack of understanding of how differentiation determinations are made, and no tools for controlling and promoting these determinations for therapeutic advantages have not been developed. Advances in these fields can explore a variety of new therapies for individuals with impaired muscle mass or functions or resolve the imbalance between muscle and adipose tissues.

In the present disclosure, the muscle disease may be selected from the group consisting of sarcopenia, amyotrophy, cancer cachexia, muscle injury, muscular dystrophy, atrophy of heart, atony, muscular dystrophy, muscular degeneration, and myasthenia, but is not limited thereto, and includes all of muscle diseases related to muscle loss.

Sarcopenia was first named by Rosenberg in 1989, and the term sarcopenia is a compound word of "sarco" meaning muscle and "penia" meaning a reduction, these being originated from Greek. In early 2017, the World Health Organization (WHO) assigned a disease classification code to sarcopenia and officially recognized it as a condition characterized by lower muscle mass than normal. Sarcopenia refers to the loss of skeletal muscle mass mainly distributed in the limbs and results from gradual loss of skeletal muscle mass associated with aging.

Amyotrophy is defined as a reduction in muscle mass. Amyotrophy is often developed when a patient is at rest, such as being in the hospital, or when a patient is restrictively moving That is, amyotrophy is often developed in cachexia where a patient is inactive or suffers from two or more diseases, such as cancer, AIDS, congestive heart failure, chronic obstructive pulmonary disease, renal failure, and severe burns. Amyotrophy is known to increase the risk of a fall and a hurt from a fall and decrease energy consumption, which is resultantly associated with increasing the risk of obesity and metabolic diseases. The results of severe diseases, such as cancer, which is a metabolic disease, may also cause amyotrophy, and this was proved to be induced by an increase in inflammatory cytokines and activation of inflammatory signaling pathways. Similarly, an environment of obesity also increases the generation of reactive oxygen species inducing oxidative stress, induces metabolic changes, such as increased influx of fatty acids into muscle tissue and reduced fatty acid oxidation, and causes disorders in mitochondrial biosynthesis, structure, and function. These oxidative stress and influx of fatty acids in the muscle may also cause inflammation and cause amyotrophy.

In accordance with another aspect of the present disclosure, there is provided a method for alleviating, suppressing, or treating a muscle disease, the method including administering to a subject a pharmaceutical composition comprising an M3 mutant peptide as an active ingredient.

In accordance with still another aspect of the present disclosure, there is provided a composition comprising an M3 mutant peptide as an active ingredient for alleviation, suppression, prevention, or treatment of obesity.

In the present disclosure, the M3 mutant peptide is as described above.

As used herein, the term "obesity" refers to a condition in which adipose tissues are excessively accumulated in the body so as to cause health disorders.

In the development of obesity, an increase in adipose tissue mass may be due to increase in the size and number of adipocytes. The increase in cell number may result in the mobilization of pre-adipose cells from a pluripotent stem cell population or from a subpopulation of cells residing in mature white adipose tissue (WAT). Bone marrow-derived mesenchymal stem cells (BM-MSCs) may differentiate into various cell types including fat, muscle, cartilage and bone. With aging, bone marrow adipogenesis accelerates in vivo, while the bone formation ability of MSCs decreases. It has been suggested that MSC precursors may contribute to age-related body composition changes by differentiating into adipose rather than bone, which is in a reciprocal relationship state.

Fat redistribution in the elderly is associated with an increased risk of metabolic syndrome, including diabetes, hypertension, dyslipidemia, atherosclerosis, and relatively increased intra-abdominal fat. In addition, muscle aging and normal aging-related muscle performance decline occur, often with a gradual onset of sarcopenia. Skeletal muscles have self-renewal ability, but this process is not activated in the elderly. Age-related changes within skeletal muscle tissues and host environments are known to influence myoblast proliferation and fusion in response to injury in aged animals.

In accordance with another aspect of the present disclosure, there is provided a method for alleviating, suppressing, or treating obesity, the method including administering to a subject a pharmaceutical composition comprising an M3 mutant peptide as an active ingredient.

In accordance with still another aspect of the present disclosure, there is provided a composition comprising an M3 mutant peptide as an active ingredient for alleviation, suppression, prevention, or treatment of diabetes.

In the present disclosure, the M3 mutant peptide is as described above.

As used herein, the term "diabetes" refers to a chronic disease characterized by a relative or absolute shortage in insulin, causing glucose-intolerance. The term diabetes includes all types of diabetes, for example, Type 1 diabetes, Type 2 diabetes, or hereditary diabetes. Type 1 diabetes is the insulin-dependent diabetes, which is mainly caused by $\beta$-cell disruption. Type 2 diabetes is the insulin-independent diabetes, which is caused by an insufficient secretion of insulin after eating or by insulin tolerance.

In accordance with still another aspect of the present disclosure, there is provided a method for alleviating, suppressing, or treating diabetes, the method including administering a pharmaceutical composition comprising an M3 mutant peptide as an active ingredient.

As used herein, the term "comprising as an active ingredient" refers to the inclusion of an amount that is sufficient to attain the efficacy or activity of the M3 mutant peptide.

The content of the peptide as an active ingredient in the composition of the present disclosure can be appropriately adjusted depending on the type and purpose of use, patient condition, type and severity of symptom, and the like. The content may be, based on the weight of solids, 0.001 to 99.9 wt %, 0.1 to 99.9 wt %, 1 to 90.9 wt %, 0.001 to 99 wt %, 0.1 to 99 wt %, 1 to 99 wt %, 0.001 to 90 wt %, 0.1 to 90 wt %, 1 to 90 wt %, 0.001 to 80 wt %, 0.1 to 80 wt %, 1 to 80 wt %, 0.001 to 70 wt %, or 0.1 to 70 wt %, for example, 1 to 70 wt %, but is not limited thereto, and may be selected within an appropriate range by a person skilled in the art.

The composition according to the present disclosure may be administered to mammals including humans through various routes. The manner of administration may be any manner that is conventionally used. For example, the administration may be performed through an oral, dermal, intravenous, intramuscular, or subcutaneous route, and preferably, an intravenous route.

The composition of the present disclosure may be formulated in the form of: an oral formulation, such as a powder, granules, a tablet, a capsule, a suspension, an emulsion, a syrup, or an aerosol; a parenteral formulation, such as a transdermal preparation, an ointment, a suppository, or a sterile injectable solution, according to a conventional method for each case.

The composition of the present disclosure may further comprise an adjuvant, such as a pharmaceutically suitable and physiologically acceptable carrier, excipient, and diluent, in addition to the mixed extract.

Examples of the carrier, excipient, and diluent that may be contained in the composition of the present disclosure may include dextrin, crystalline cellulose, lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methyl hydroxybenzoate, propyl hydroxybenzoate, talc, magnesium stearate, and a mineral oil.

When the composition is formulated as a preparation, a diluent or excipient, such as a filler, an extender, a binder, a wetting agent, a disintegrant, or a surfactant, that are usually used may be used. Solid preparations for oral administration may include a tablet, a pill, a powder, granules, a capsule, and the like, and these solid preparations may be prepared by adding to the extract at least one excipient, for example, starch, calcium carbonate, sucrose or lactose, gelatin, or the like. In addition to simple excipients, lubricants such as magnesium stearate talc may also be used.

Preparations for oral administration correspond to a suspension, a liquid preparation, an emulsion, a syrup, and the like, and may comprise simple diluents that are frequently used, such as water and liquid paraffin, as well as several types of excipients, such as a humectant, a sweetener, an aroma, and a preservative.

Preparations for parenteral administration include a sterilized aqueous solution, a non-aqueous solvent, a suspension, an emulsion, a lyophilized agent, a suppository, a transdermal agent, and the like. Examples of the non-aqueous solvent and suspension may include propylene glycol, polyethylene glycol, a vegetable oil such as olive oil, an injectable ester such as ethylolate, and the like.

Examples of a substrate for the suppository may include Witepsol, Macrogol, Tween 61, cacao butter, laurin butter, glycerogelatin, and the like.

In an embodiment to which the composition of the present disclosure is applied to humans, the pharmaceutical composition of the present disclosure may be administered alone, but may be generally administered by mixing with a pharmaceutical carrier selected considering the manner of administration and standard pharmaceutical practice.

For example, the pharmaceutical composition of the present disclosure may be administered orally, intrabuccally, sublingually, in the form of a tablet comprising starch or lactose, in the form of a capsule with or without excipient; or in the form of an elixir or suspension comprising a chemical making a flavor or displaying a color.

These liquid preparations may be formulated with pharmaceutically acceptable additives, such as a suspension (for example, semi-synthesized glyceride such as methylcellulose, Witepsol, or a glyceride mixture such as a mixture of apricot kernel oil and PEG-6 ester or a mixture of PEG-8 and caprylic/capric glyceride).

The dose of the pharmaceutical composition of the present disclosure may vary depending on the age, body weight, sex of a patient, administration form, health condition, and severity of a disease, and may be divisionally administered at regular intervals according to the determination of the doctor and pharmacist.

For example, the daily dose, on the basis of the content of the active ingredient, may be 0.1 to 1000 mg/kg, 0.1 to 900 mg/kg, 0.1 to 800 mg/kg, 0.1 to 700 mg/kg, or 0.1 to 600 mg/kg, for example, 0.5 to 500 mg/kg. The dose is illustrative of the average case, and may be higher or lower depending on individual differences.

A daily dose of the pharmaceutical composition of the present disclosure, which is less than the above-described dose, cannot provide a significant effect, and a daily dose exceeding the above-described dose range is non-economical, and is out of the normal dose range and thus may cause an undesirable side effect, and therefore the above range is preferable.

Advantageous Effects of Invention

The present disclosure relates to an M3 mutant peptide, a composition comprising the same as an active ingredient for alleviation, suppression, prevention, or treatment of a muscle disease, obesity, or diabetes, a method for alleviating, suppressing, preventing, or treating a muscle disease, obesity, or diabetes, by using an M3 mutant peptide, and use of an M3 mutant peptide for alleviating, suppressing, preventing, or treating a muscle disease, obesity, or diabetes.

Figure 10:
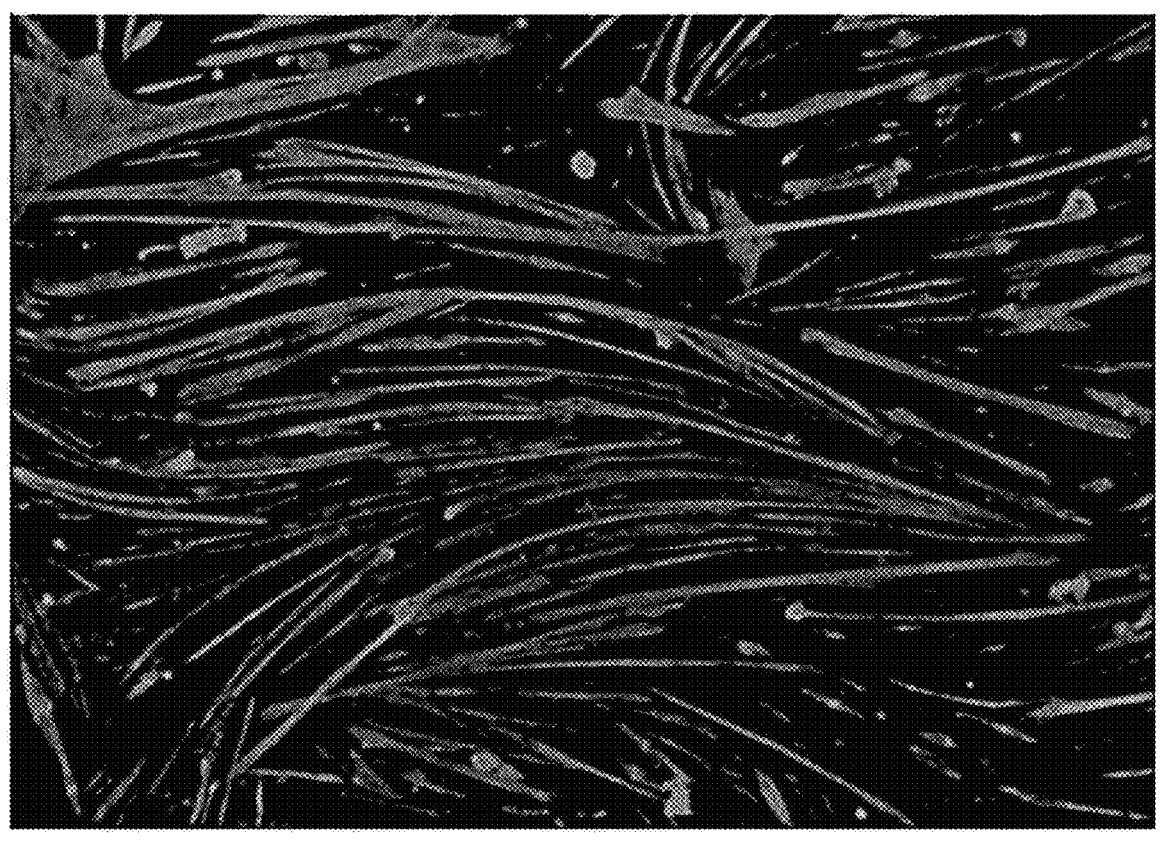

FIG. 10 presents an image showing the results of examining the length of differentiation-induced myotubes of an M5 mutant through immunofluorescence staining according to an exemplary embodiment of the present disclosure.

Figure 11:
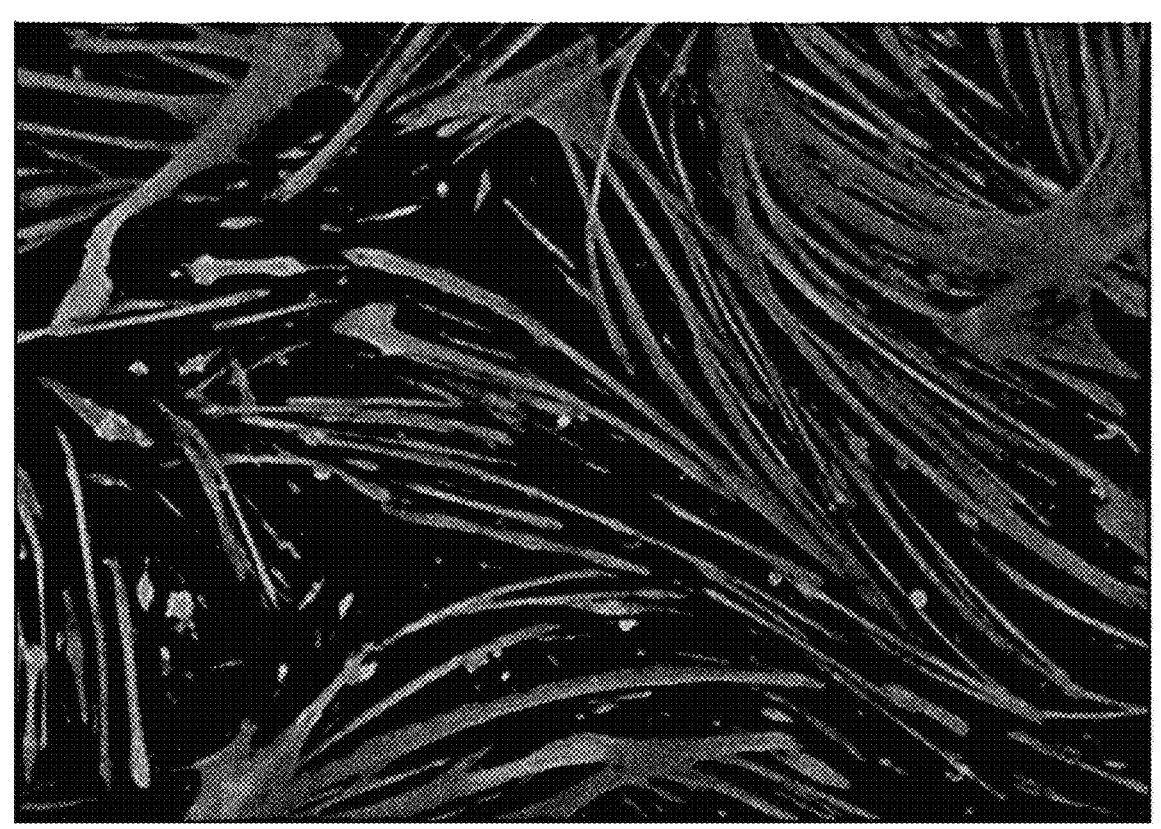

FIG. 11 presents an image showing the results of examining the length of differentiation-induced myotubes of an M6 mutant through immunofluorescence staining according to an exemplary embodiment of the present disclosure.

Figure 12:
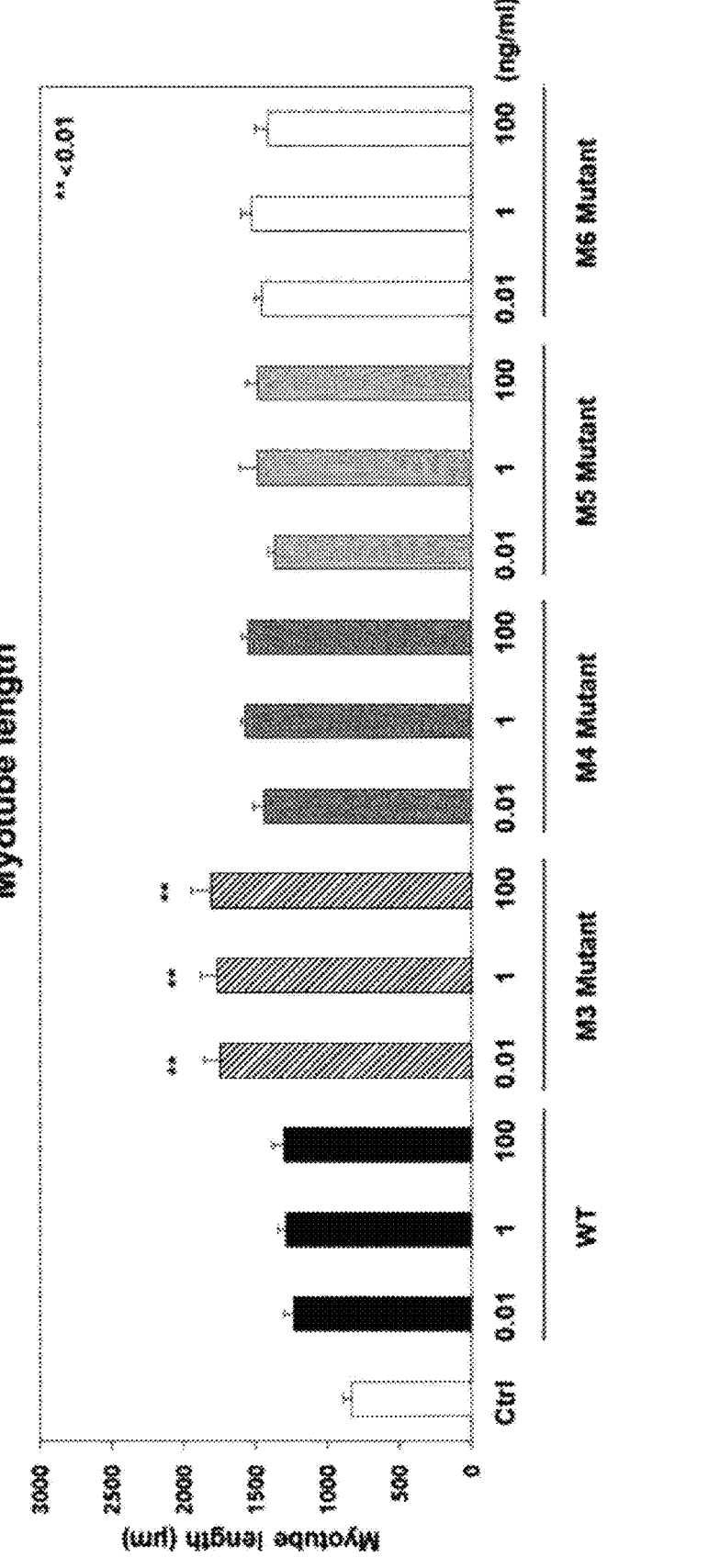

FIG. 12 presents a graph showing the results of examining the length of differentiation-induced myotubes through immunofluorescence staining according to an exemplary embodiment of the present disclosure.

Figure 13:
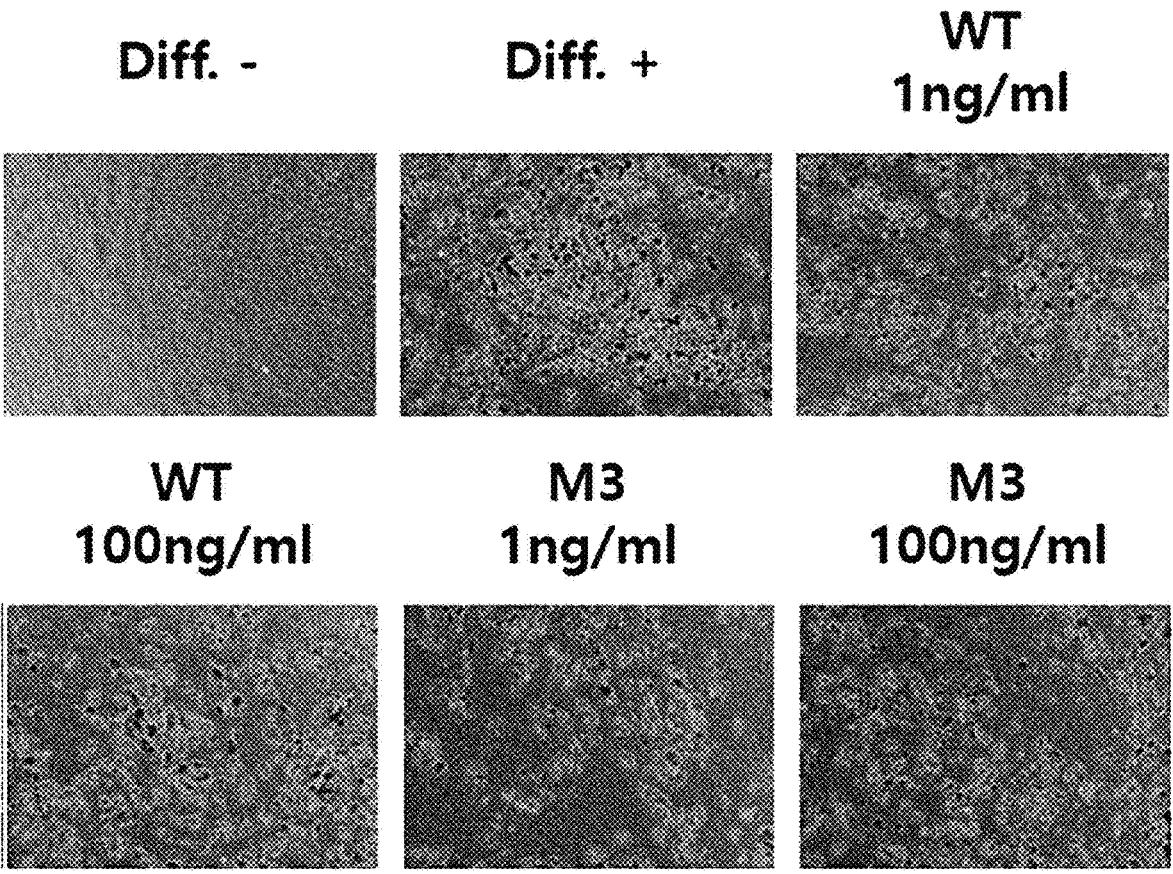

FIG. 13 presents images showing the results of differentiation of adipose-derived mesenchymal stem cells into adipocytes according to an exemplary embodiment of the present disclosure.

Figure 14:
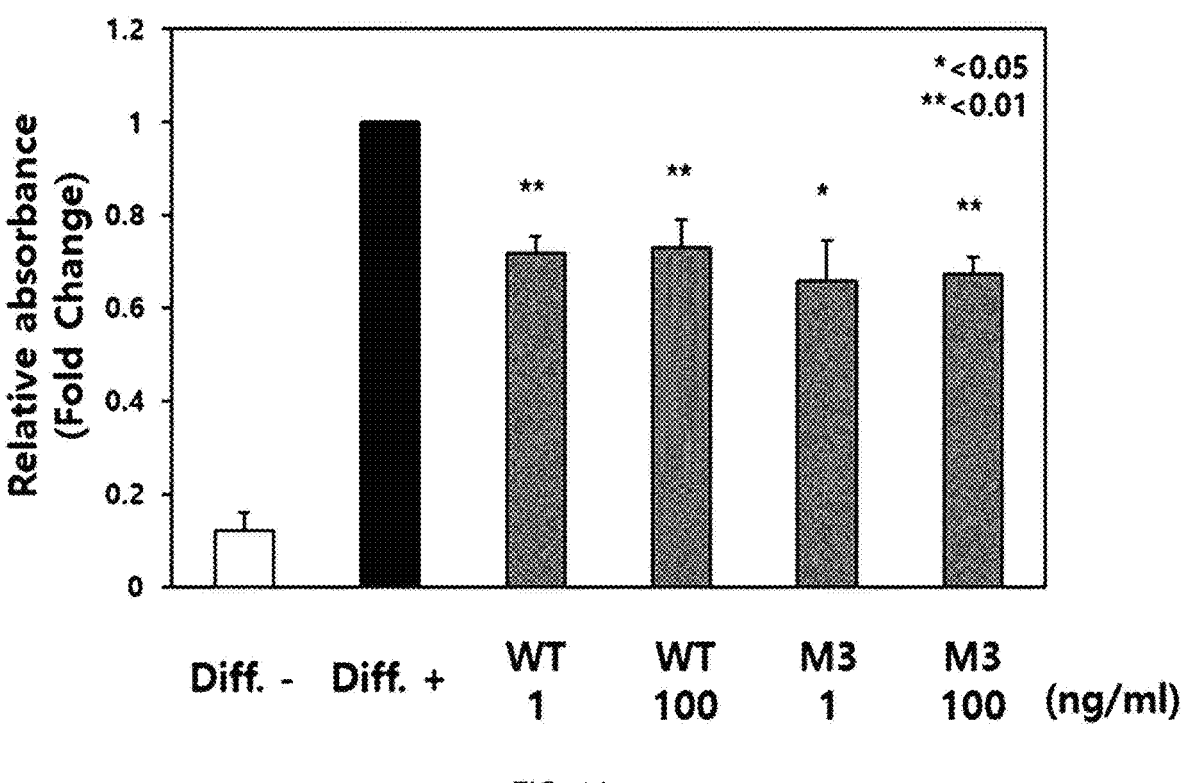

FIG. 14 presents a graph showing the results of examining the extent of adipogenesis according to an exemplary embodiment of the present disclosure.

Figure 15:
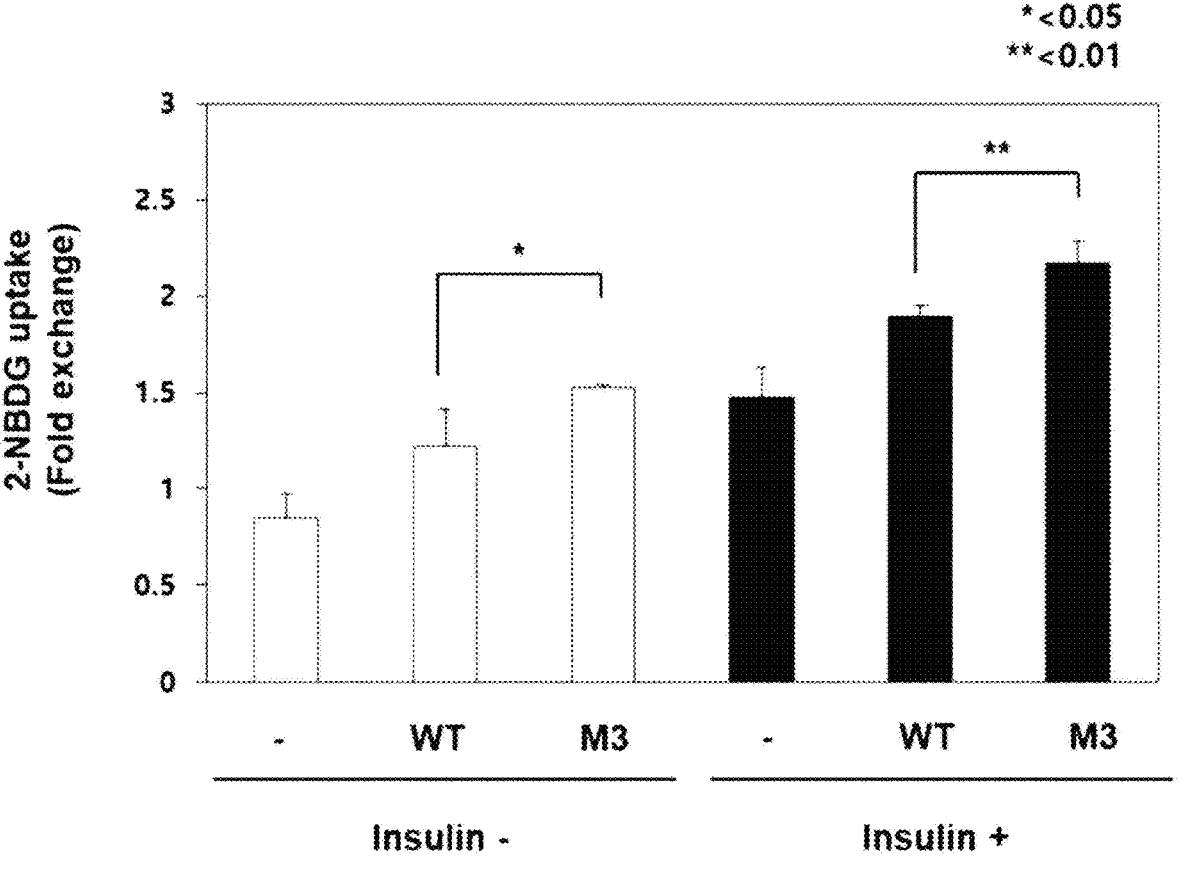

FIG. 15 presents a graph showing the results of measuring intracellular glucose uptake according to an exemplary embodiment of the present disclosure.

Figure 16:
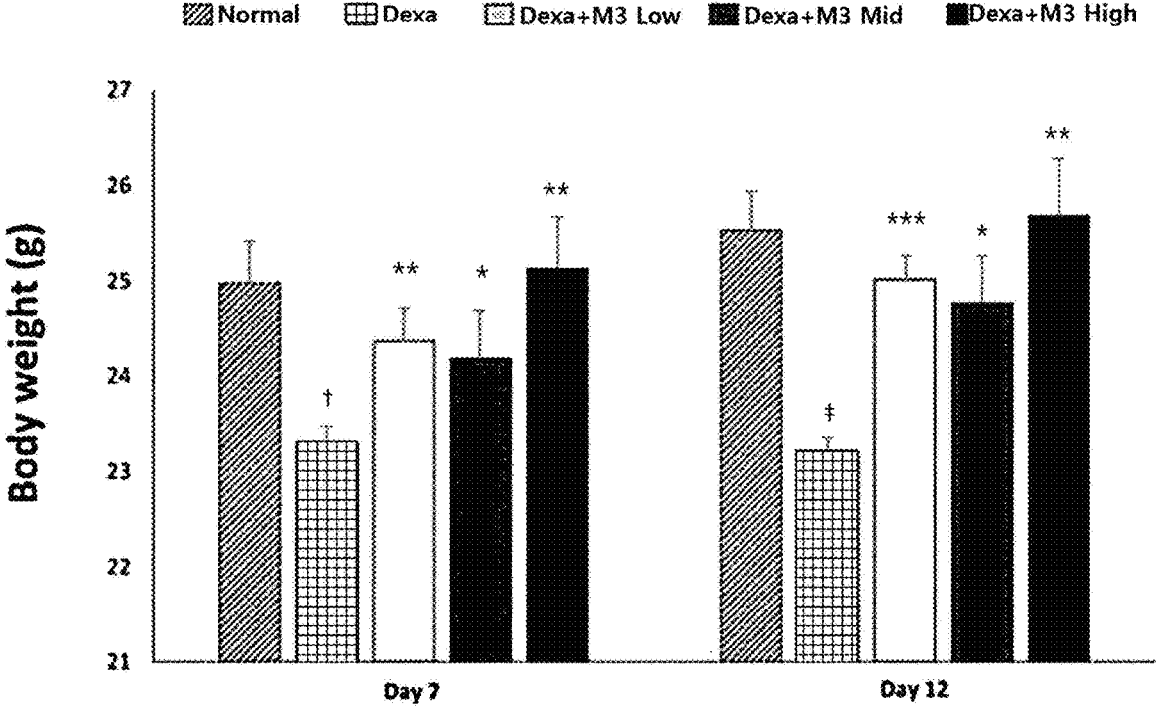

FIG. 16 presents a graph showing body weight changes in a muscle loss animal model according to an exemplary embodiment of the present disclosure.

Figure 17:
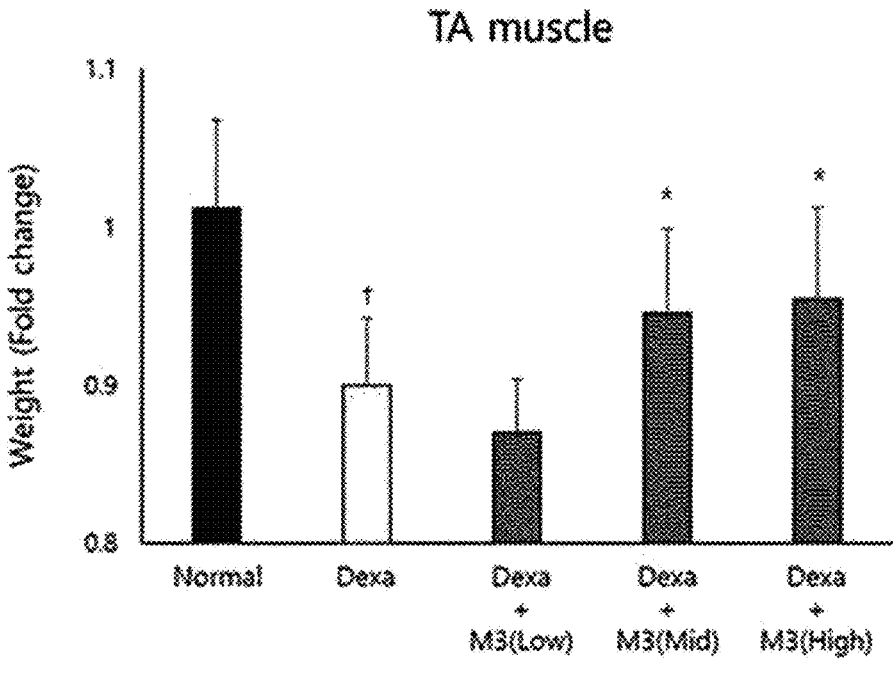
Figure 17:
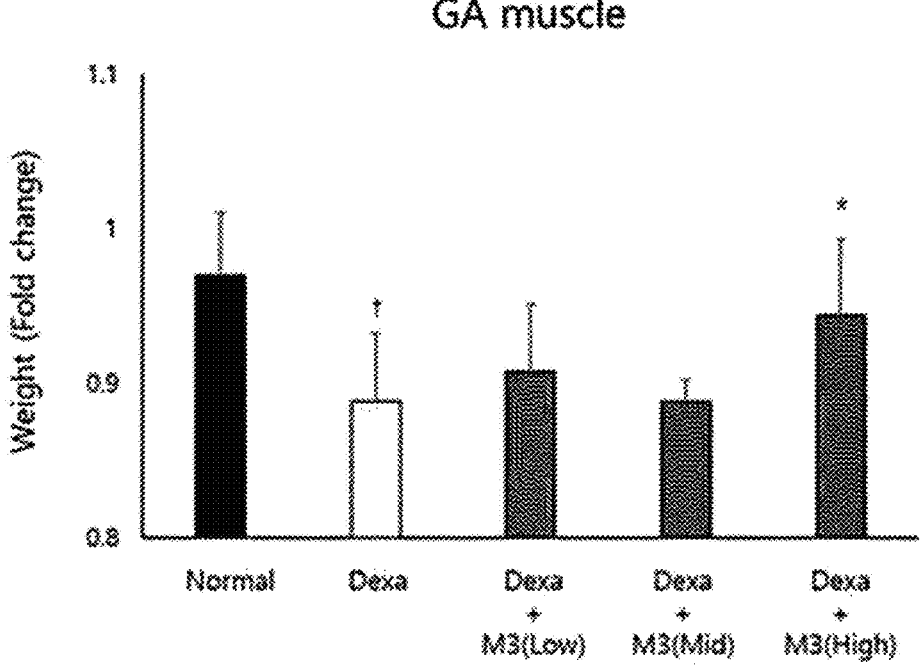

FIG. 17 presents graphs showing the results of body weight changes of GA and TA muscle tissues in a muscle loss animal model according to an exemplary embodiment of the present disclosure.

Figure 18:
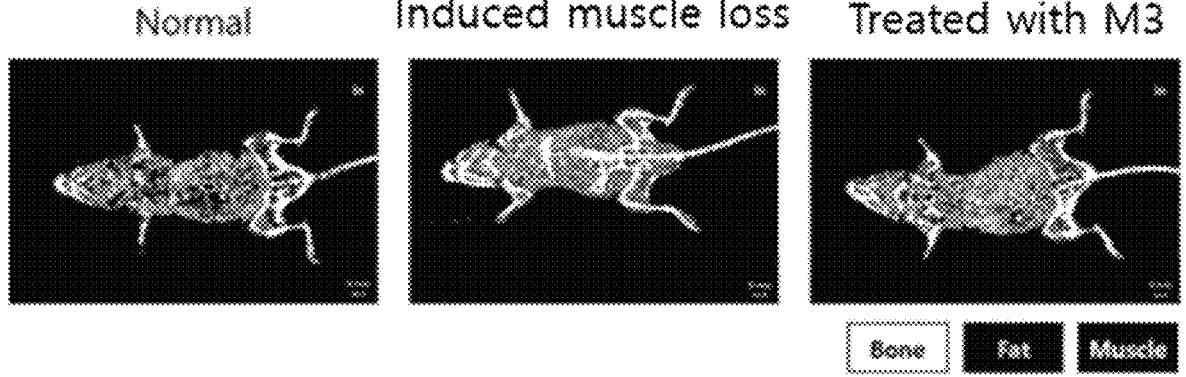
Figure 18:
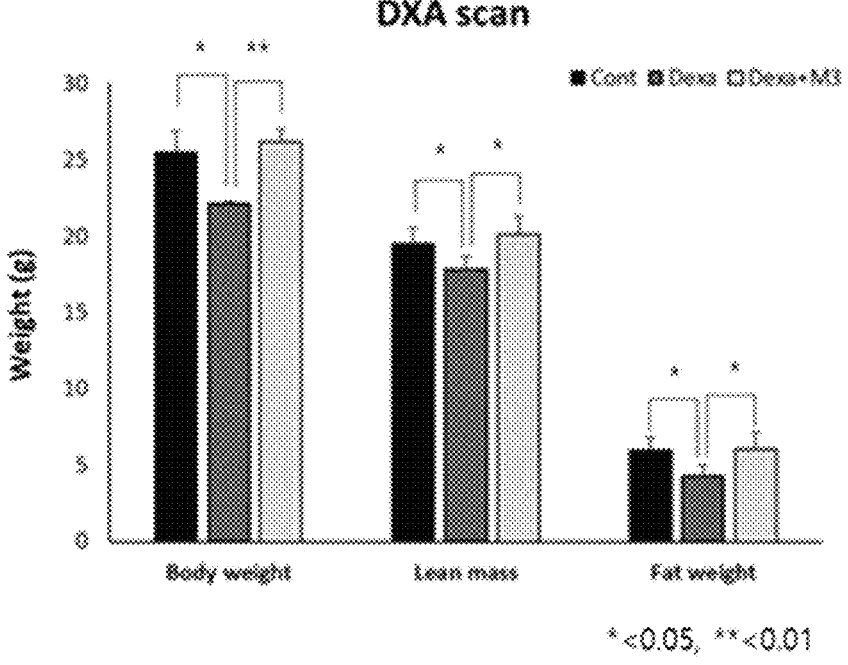

FIG. 18 presents a graph showing fat and muscle weight changes in a muscle loss animal model according to an exemplary embodiment of the present disclosure.

Figure 19:
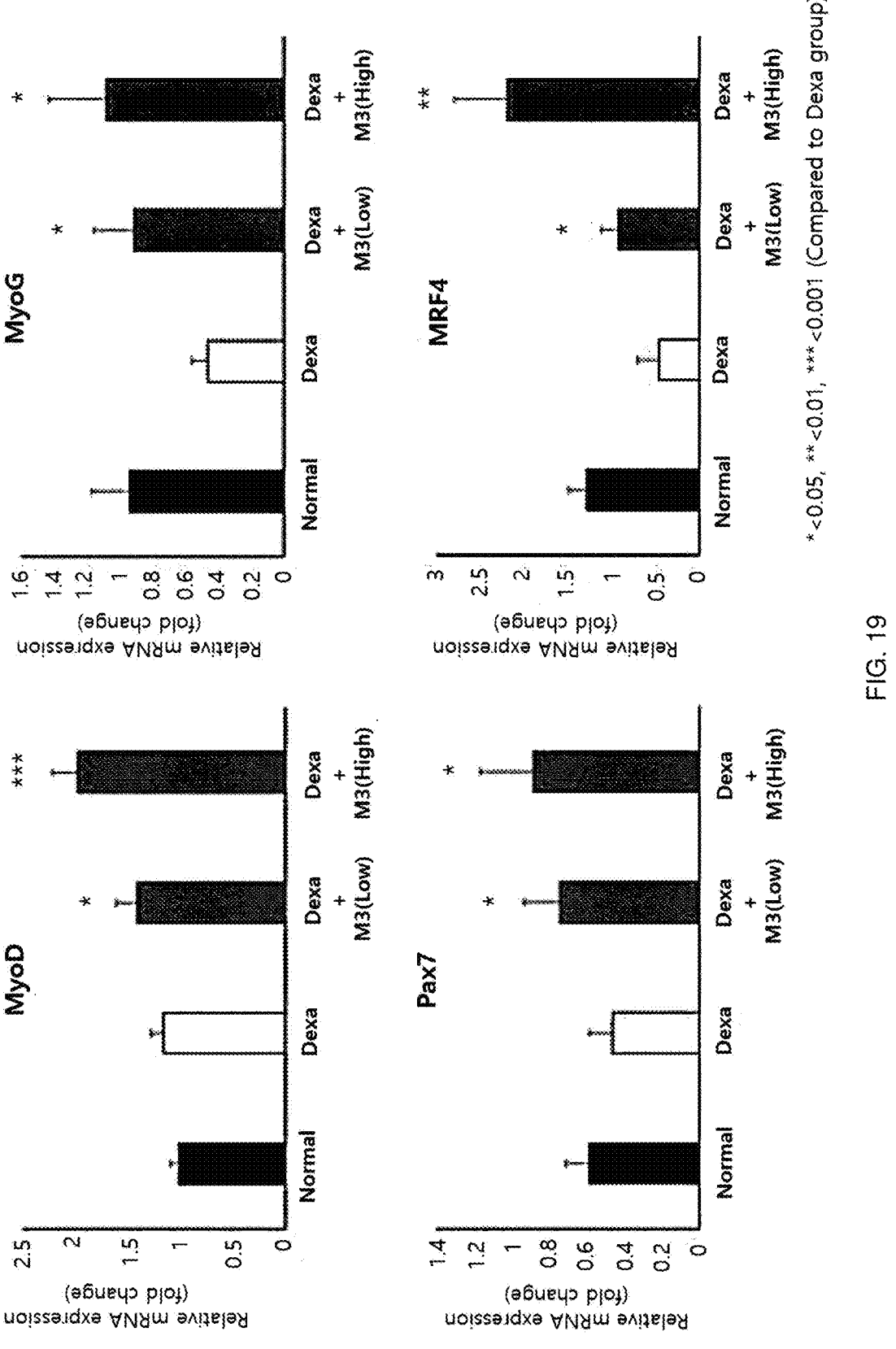

FIG. 19 presents graphs showing the results of examining expression levels of MyoD, MyoG, Pax7, and MRF4 genes, which are muscle differentiation-related genes, according to an exemplary embodiment of the present disclosure.

Figure 20:
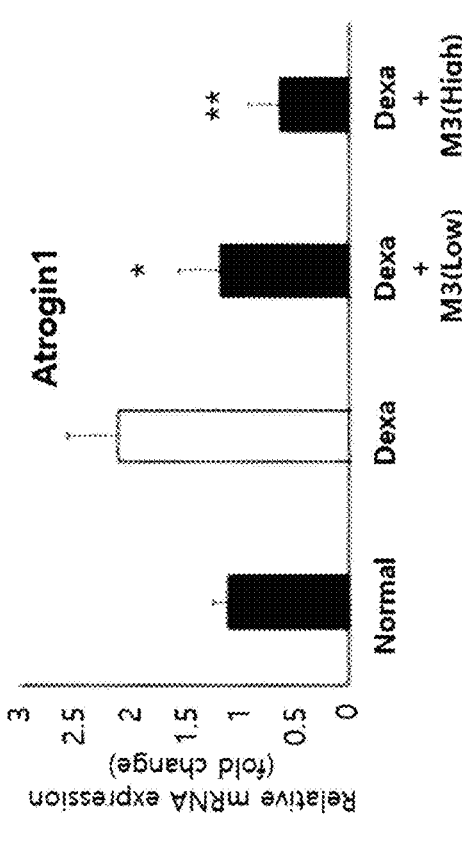
Figure 20:
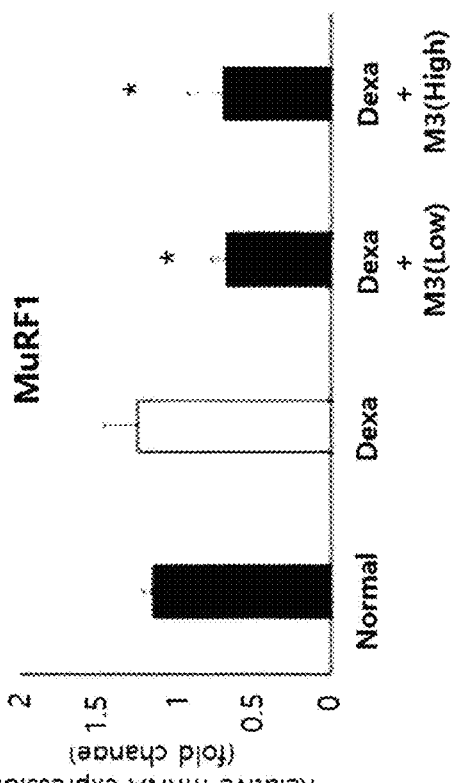
Figure 20:
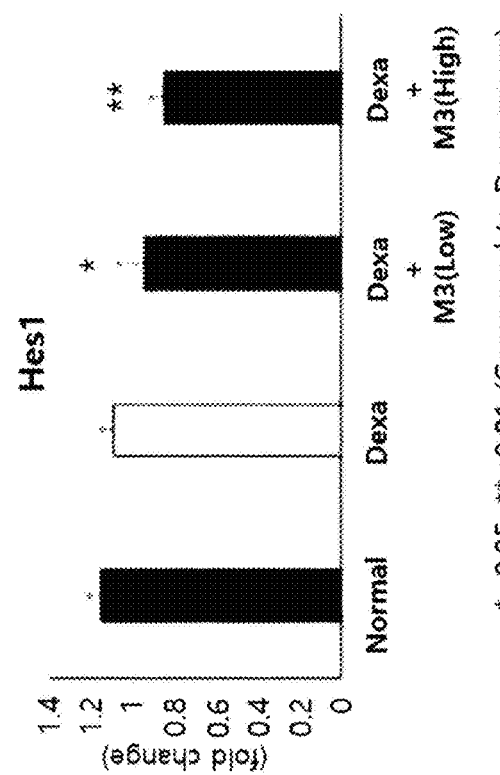

FIG. 20 presents graphs showing the results of examining expression levels of MuRF1, Atrogin1, and Hes1, which are muscle differentiation inhibition-related genes, according to an exemplary embodiment of the present disclosure.

Figure 21:
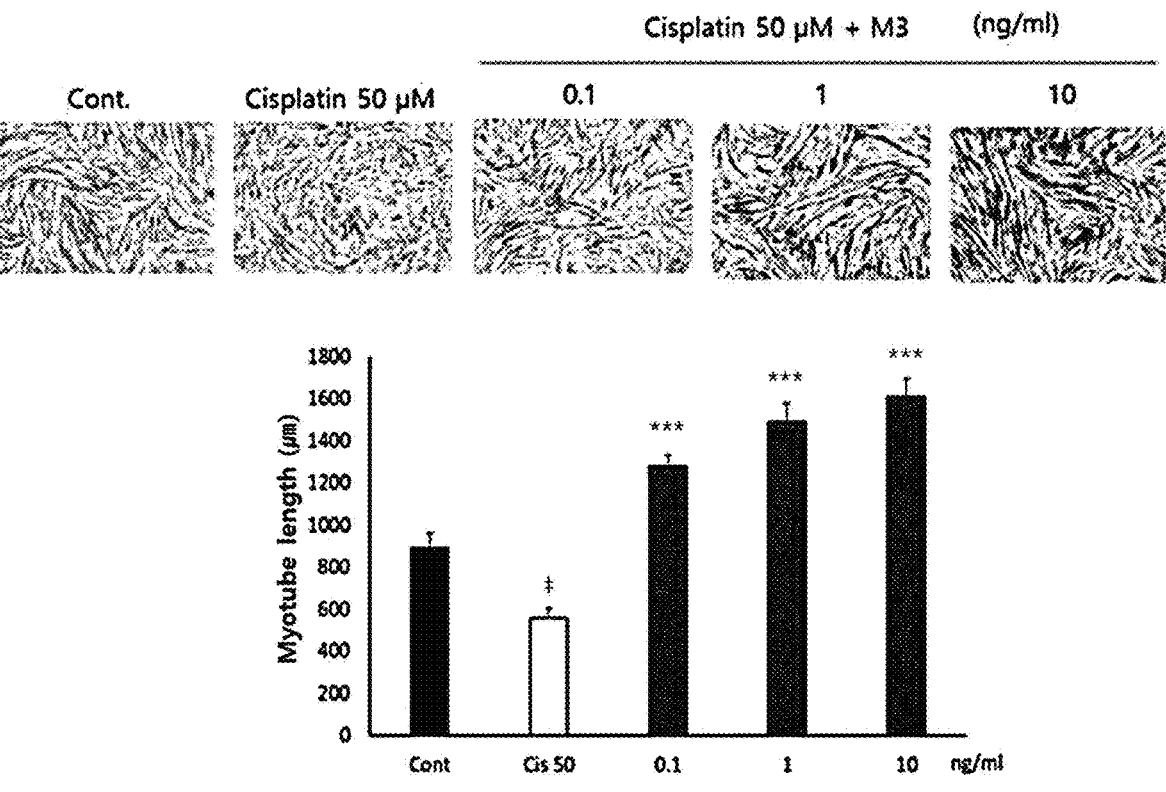

FIG. 21 presents a graph showing the results of examining the length of differentiation-induced myotubes through Jenner's staining according to an exemplary embodiment of the present disclosure.

Figure 22:
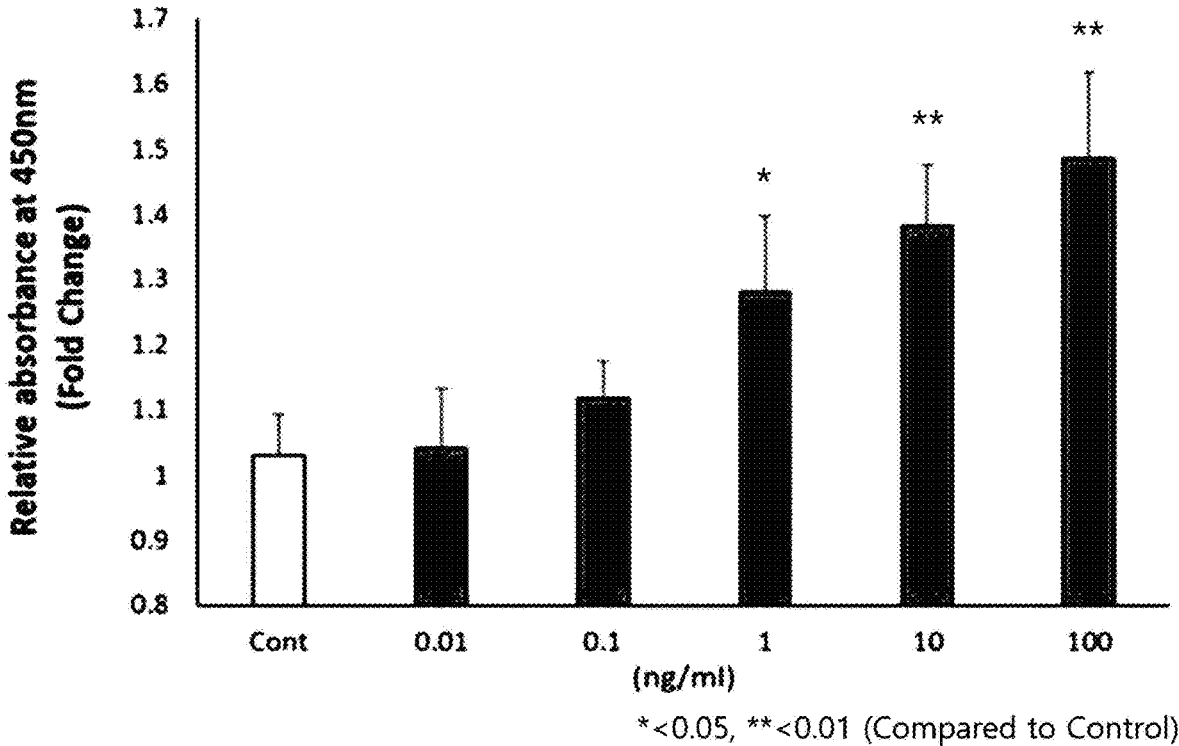

FIG. 22 presents a graph showing the results of examining the extent of activity of myocytes according to an exemplary embodiment of the present disclosure.

BEST MODE FOR CARRYING OUT THE INVENTION

Hereinafter, the present disclosure will be described in more detail with reference to exemplary embodiments. These exemplary embodiments are provided only for the purpose of illustrating the present disclosure in more detail, and therefore, according to the purpose of the present disclosure, it would be apparent to a person skilled in the art that these exemplary embodiments are not construed to limit the scope of the present disclosure.

EXAMPLES

Example 1: Culture and Differentiation Induction of C2C12 Cell Line

C2C12 cell line (ATCC, CRL-1772), a myoblast cell line mainly used for myocyte differentiation research, was cultured in DMEM supplemented with 10% fetal bovine serum (FBS), 100 U/ml penicillin, and 100 μg/ml streptomycin, as a culture medium, in a cell incubator at 37° C. supplied with 5% $CO_2$.

The C2C12 cell line was inoculated into 24-well cell culture plates at $5 \times 10^4$/well and cultured in the culture medium. When the cells reached a density of 90% in the cell culture plates, the medium was replaced with DMEM comprising 2% horse serum as a differentiation medium and differentiation was induced. The differentiation medium was newly replaced at intervals of 3 days, and differentiation was induced in a cell incubator at 37° C. supplied with 5% $CO_2$ for a total of 8 days.

ADAMTS1 and mutant ADAMTS1 recombinant proteins produced in CHO-K1 cell line were subjected to isolate and purification by the method as in Example 2 below, and were used to treat the C2C12 cell line at concentrations of 0.01, 0.1, 1, 10, and 100 ng/ml once a day from the start of differentiation induction to the end of differentiation induction.

Example 2: Production of Recombinant Protein

For isolation and purification of the recombinant proteins produced in the cells, ADAMTS1 overexpression vector was constructed so that 6×His was attached to the C-terminus of the recombinant proteins. Specifically, pEF6/V5-His A vector (Invitrogen, V96120) was digested with KpnI and XhoI restriction enzymes. The sequence recognized by KpnI was inserted at the 5' end of the CDS part of the ADAMTS1 sequence (NM_006988.5) and the sequence recognized by XhoI was inserted at the 3' end thereof, and then ligation to the previously digested vector was conducted using T4 DNA ligase. M1, M2, M3, M4, M5, and M6 mutant ADAMTS1 were constructed using wild-type ADAMTS1 as a template while starting from nucleotide number 664, nucleotide number 664-693 for M1, nucleotide number 664-723 for M2, nucleotide number 664-753 for M3, nucleotide number 664-783 for M4, nucleotide number 664-813 for M5, and nucleotide number 664-843 for M6 were cleaved, respectively, and in all the mutants, the sequences after nucleotide number 1237 were removed.

The CHO-K1 cell line was inoculated in 6-well cell culture plates using RPMI 1640 medium supplemented with 10% fetal bovine serum (FBS), 100 U/ml penicillin, 100 μg/ml streptomycin, and 25 mM HEPES as a culture medium and cultured in a cell incubator at 37° C. supplied with 5% $CO_2$. The next day, Lipofectamine 2000 (Invitrogen, 11668019) was mixed with the ADAMTS1 or ADAMTS1 mutant expression vectors and used to treat the CHO-K1 cells to introduce the vectors into the cells. After culturing for 24 hours, the cells were diluted 10-fold, transferred to 100 mm cell culture dishes, and then first treated with Blasticidin-S™ at a concentration of 10 μg/ml. Thereafter, the medium was replaced with a new culture medium mixed with Blasticidin-S™ at a concentration of 10 μg/ml a total of three times at intervals of 4 days. After independent colonies were formed by Blasticidin-S™, each colony was inoculated into new cell culture plates and cultured. Each colony was examined for whether ADAMTS1 or ADAMTS1 mutant proteins were expressed, through western blotting, and then used as a stabilized cell line. The CHO-K1 stabilized cell line was inoculated into 100 mm dishes, and when the cell density reached 100%, the medium was replaced with RPMI 1640 medium and cultured for 2 days. After 2 days, only the upper part of the culture was taken from the cultured dishes, purified with Ni-NTA agarose (Qiagen, 30210), recovered, and used for differentiation induction experiments of the C2C12 cell line. Specifically, the cell culture was passed through a gravity chromatography column (Qiagen, 34964) equipped with Ni-NTA agarose and then washed with 10 mM imidazole buffer. After repeated three times of washing, the proteins were purified by elution with 250 mM imidazole buffer.

Example 3: Expression of Recombinant Proteins

Figure 1A:
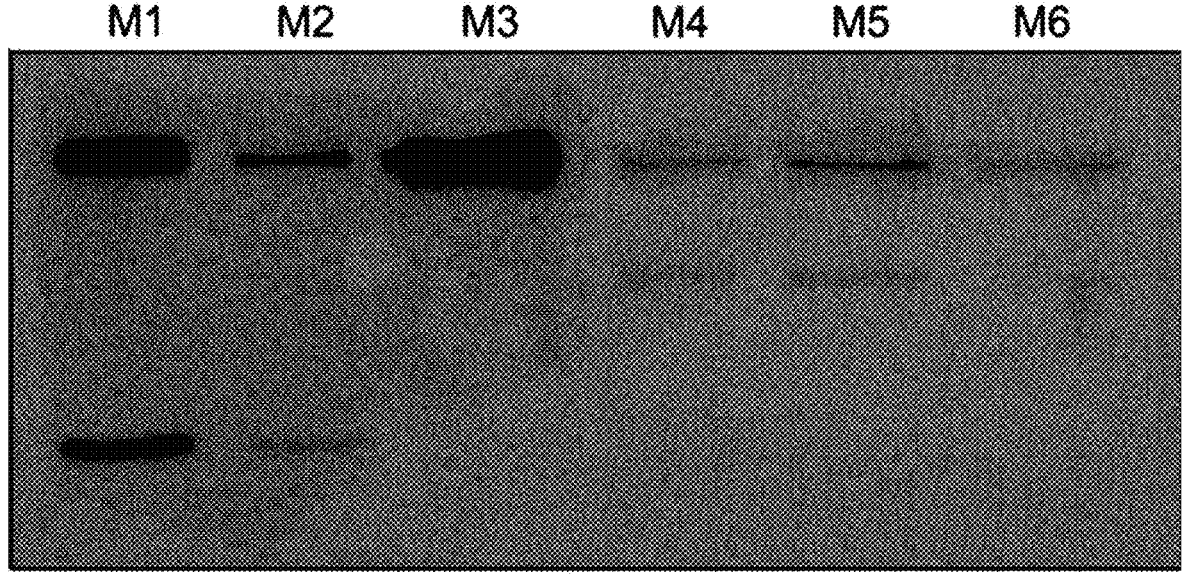
FIG. 1A presents an image showing the results of examining the expression of mutant peptides through western blotting according to an exemplary embodiment of the present disclosure.

The culture of the ADAMTS1 mutant-overexpressed CHO-K1 stabilized cell line prepared by the method as in Example 2 was taken and examined for the expression of the constructed recombinant proteins through western blotting using an antibody recognizing 6×-His. The results are shown in FIGS. 1A and 1B.

Figure 1B:
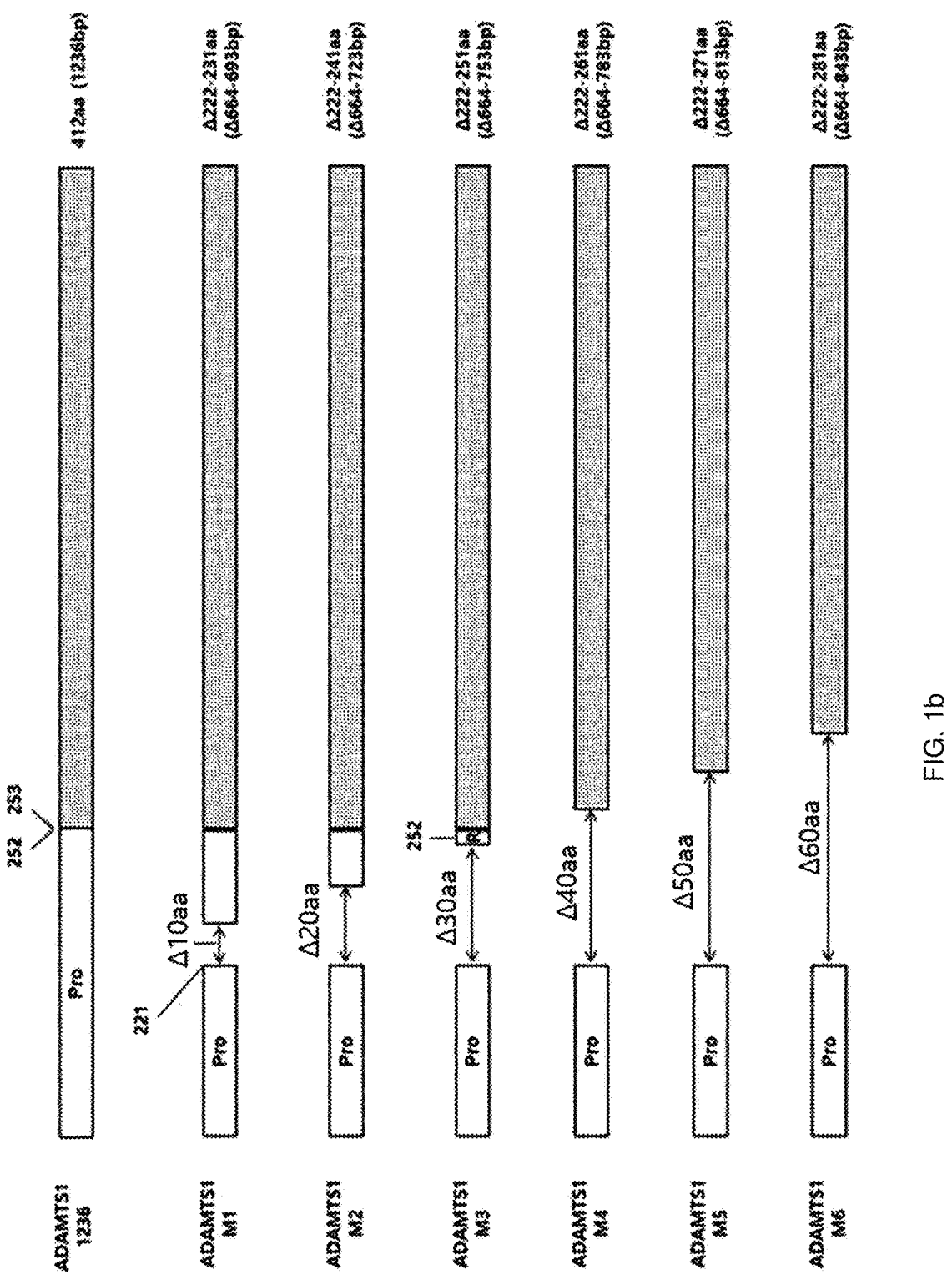
FIG. 1B presents a schematic diagram of mutant peptides according to an exemplary embodiment of the present disclosure.
Figure 2:
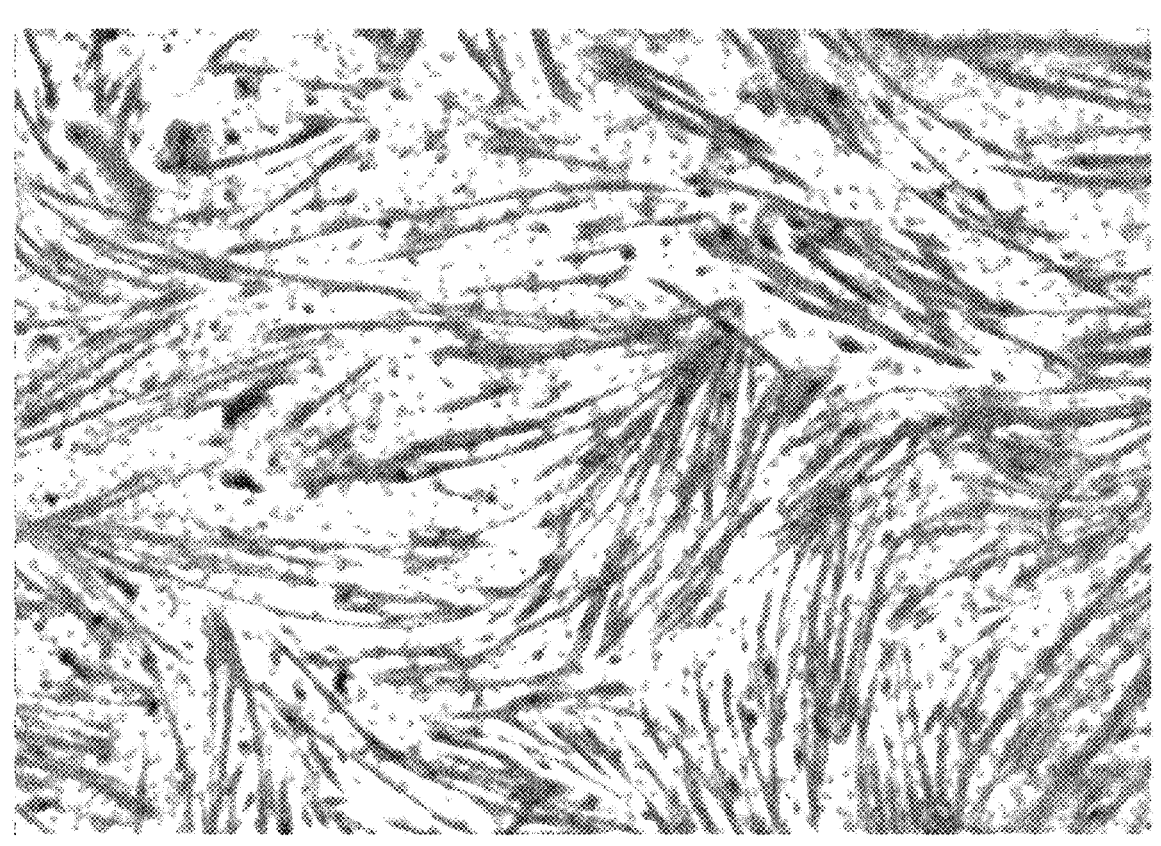
FIG. 2 presents the results of examining the length of differentiation-induced myotubes of a control group through Jenner's staining according to an exemplary embodiment of the present disclosure.
Figure 3:
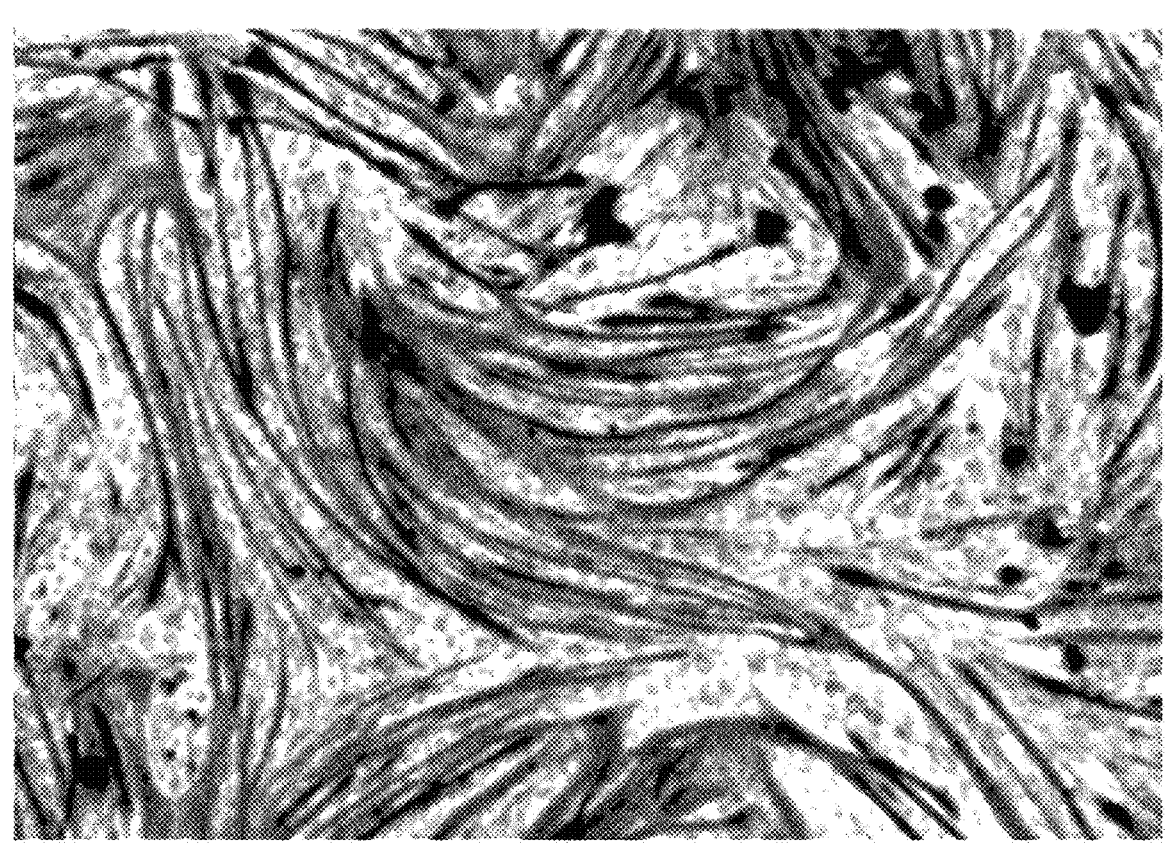
FIG. 3 presents the results of examining the length of differentiation-induced myotubes of a wild type through Jenner's staining according to an exemplary embodiment of the present disclosure.
Figure 4:
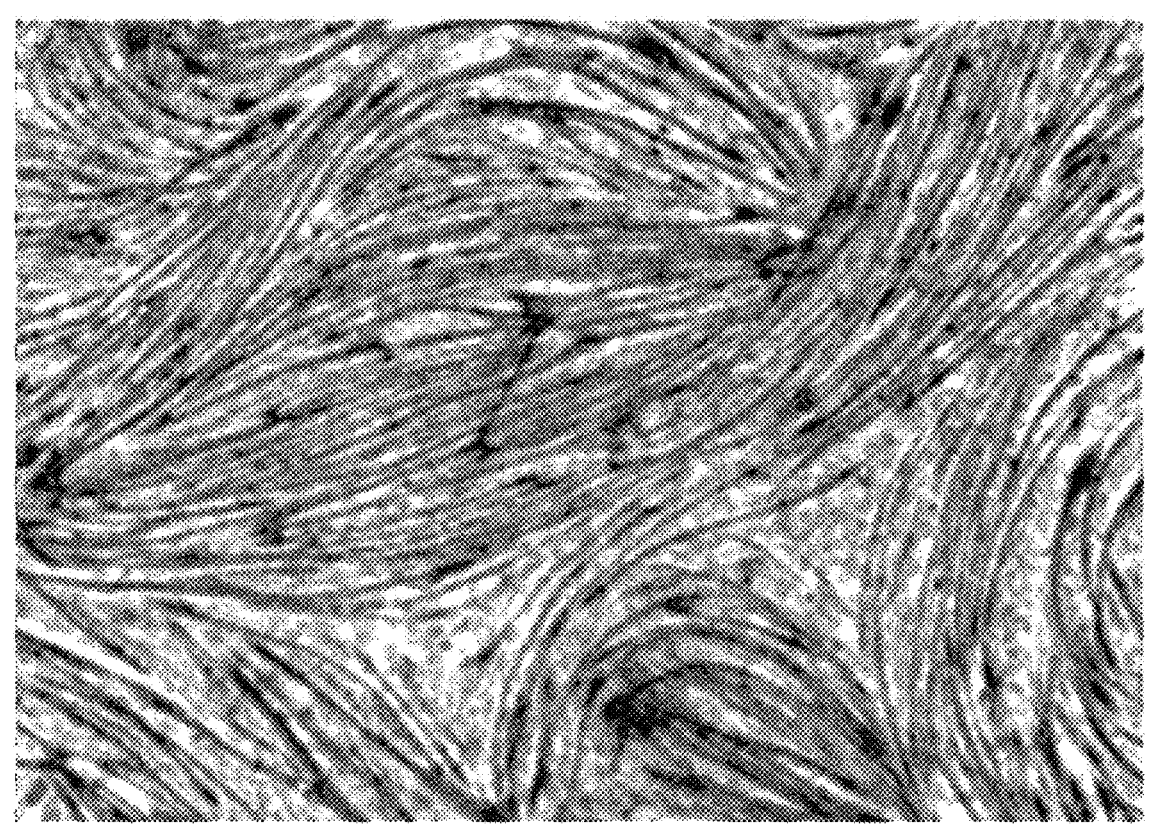
FIG. 4 presents the results of examining the length of differentiation-induced myotubes of an M3 mutant through Jenner's staining according to an exemplary embodiment of the present disclosure.
Figure 5:
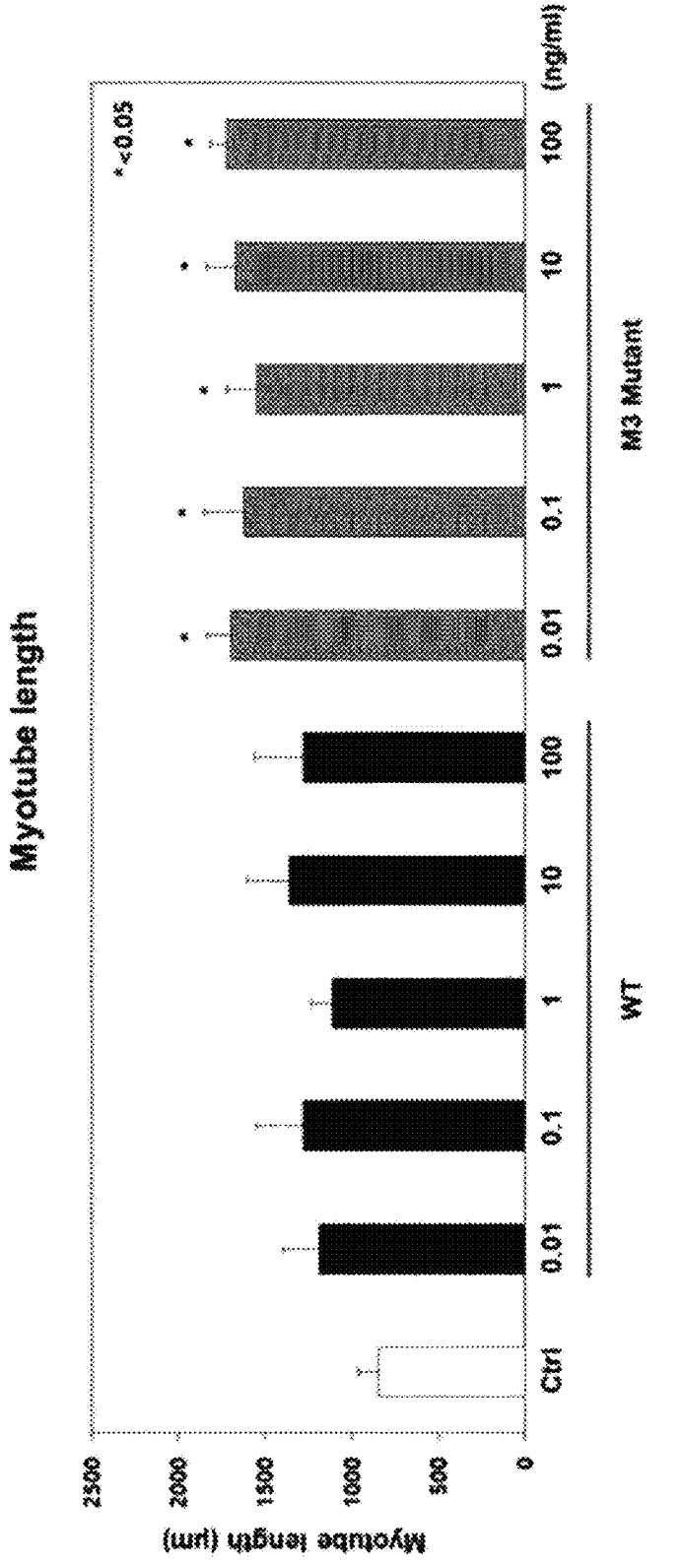
FIG. 5 presents a graph showing the results of examining the length of differentiation-induced myotubes through Jenner's staining according to an exemplary embodiment of the present disclosure.
Figure 6:
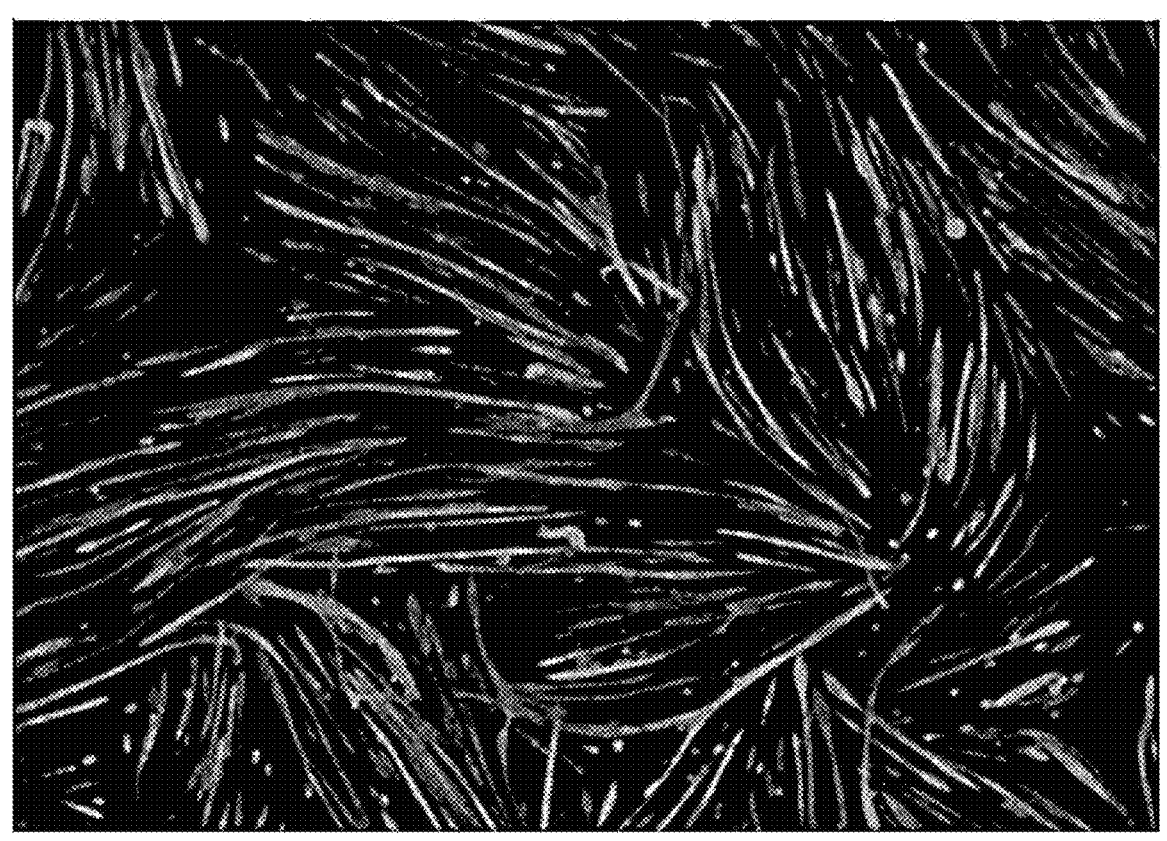
FIG. 6 presents an image showing the results of examining the length of differentiation-induced myotubes of a control group through immunofluorescence staining according to an exemplary embodiment of the present disclosure.
Figure 7:
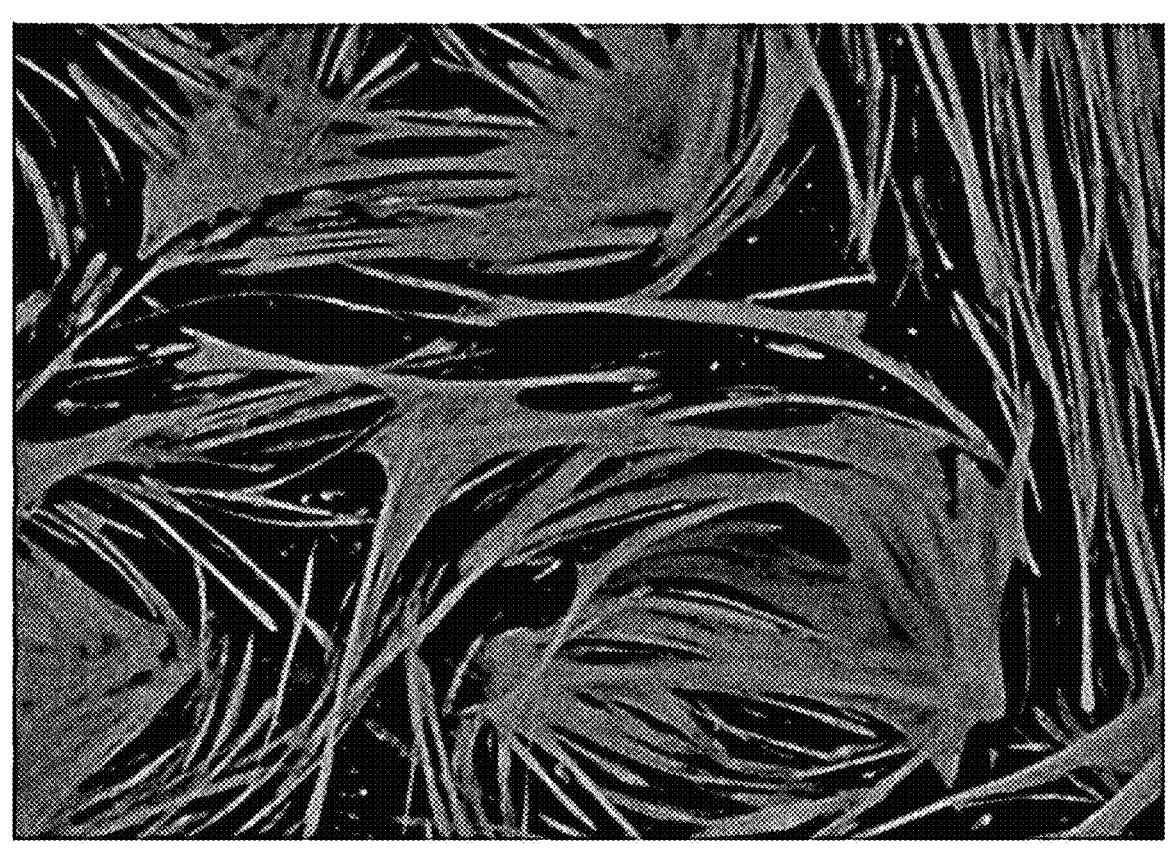
FIG. 7 presents an image showing the results of examining the length of differentiation-induced myotubes of a wild type through immunofluorescence staining according to an exemplary embodiment of the present disclosure.
Figure 8:
FIG. 8 presents an image showing the results of examining the length of differentiation-induced myotubes of an M3 mutant through immunofluorescence staining according to an exemplary embodiment of the present disclosure.
Figure 9:
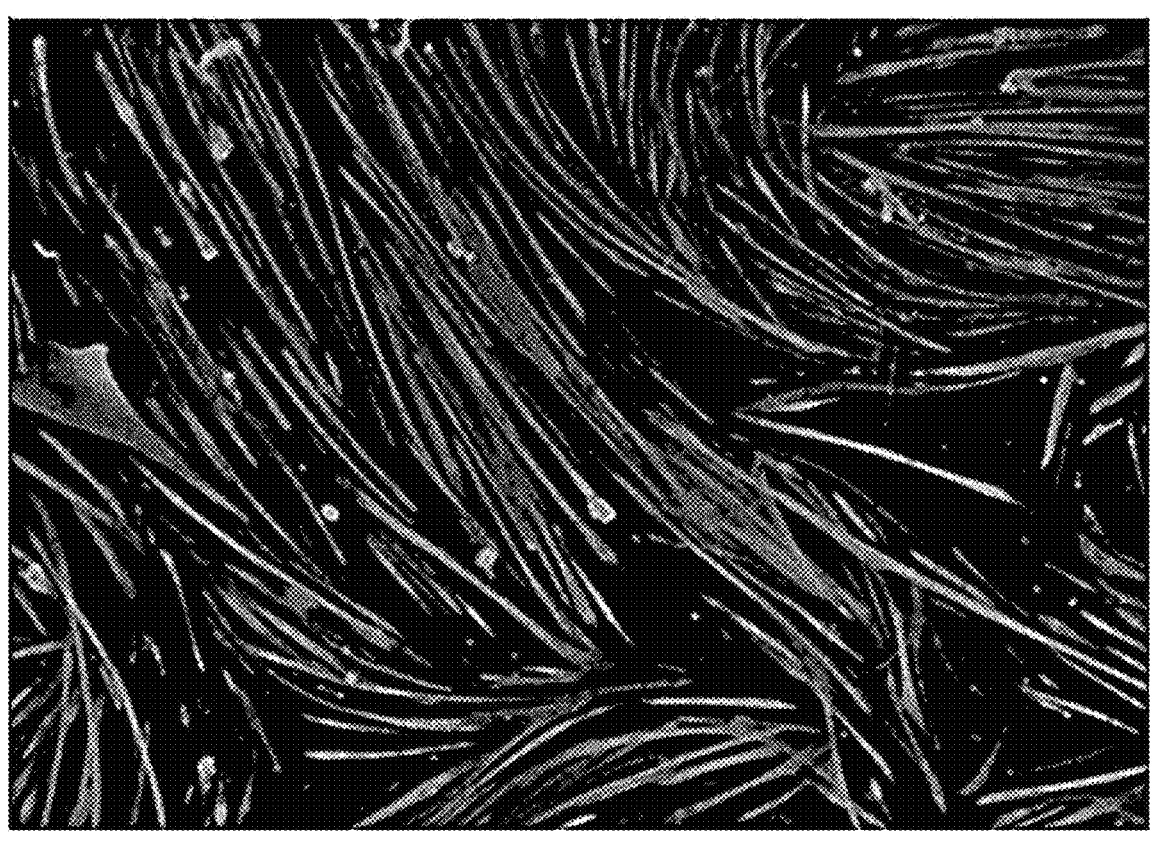
FIG. 9 presents an image showing the results of examining the length of differentiation-induced myotubes of an M4 mutant through immunofluorescence staining according to an exemplary embodiment of the present disclosure.

As can be confirmed from FIG. 1B, M1 and M2 mutants showed that two types of proteins, a part comprising pro-domain and a mature domain, were all expressed, but M3, M4, M5, and M6 mutants showed that only a protein comprising a pro-domain was expressed. Out of the mutants expressing only the protein comprising a pro-domain, the others except for M3 mutant showed reduced expression (see FIG. 1A).

Example 4: Jenner's Staining

The C2C12 cell line was treated with ADAMTS1 or ADAMTS1 mutant recombinant protein while being differentiation-induced in 24-well culture plates for 8 days. The differentiation-induced cells were fixed in methanol for 10 minutes. The plates were sufficiently washed with PBS three times, and then stained for 10 minutes with a mixture of 2.5 mg/ml of Jenner staining reagent dissolved in methanol and distilled water at 1:1. The stained plates were washed with distilled water, followed by drying, and then observed under a microscope. The results are shown in FIGS. 2 to 5 and Table 1.

TABLE 1

| Classification | ng/ml | Mean (um) | SD |
|---|---|---|---|
| Ctrl | — | 840.5593 | 122.843 |
| WT | 0.01 | 1187.7 | 209.7841 |
| | 0.1 | 1279.783 | 270.5997 |
| | 1 | 1110.381 | 122.6237 |
| | 10 | 1361.083 | 238.143 |
| | 100 | 1276.93 | 279.3668 |
| M3 mutant | 0.01 | 1698.274 | 133.7239 |
| | 0.1 | 1618.237 | 230.9828 |
| | 1 | 1545.182 | 174.167 |
| | 10 | 1669.126 | 169.7136 |
| | 100 | 1718.463 | 94.99775 |

As can be confirmed from FIGS. 2 to 5 and Table 1, the co-treatment of C2C12 cell line with ADAMTS1 during the differentiation induction of the cells resulted in an increase in myotube length, and especially, the treatment with M3 mutant showed a more increase in myotube length compared with the differentiation-induced cell line treated with the wild type.

Example 5: Immunofluorescence Staining

The C2C12 cell line treated with ADAMTS1 or ADAMTS1 mutant recombinant proteins while being differentiation-induced in 24-well culture plates for 8 days. The differentiation-induced cells were fixed in 4% formaldehyde for 10 minutes and then subjected to cell membrane permeabilization for 10 minutes by using 0.25% Triton X-100.

Thereafter, the plates were blocked with 2% BSA for 30 minutes, and then treated for 1 hour with the myosin heavy chain (MHC) antibody mixed with 2% BSA buffer at 1:500. Then, the cells were treated for 1 hour with Alexa Fluor® 555 fluorescence antibody mixed with 2% BSA at 1:200, and nuclei were stained through DAPI staining.

The stained plates were photographed using a fluorescence microscope (Nikon Ts2-FL), and the length of myotubes was measured using an analysis program (Nikon, NIS Elements) provided by the manufacturer and statistically processed. The analyzed plates were shielded from light and stored in a refrigerator. The results are shown in FIGS. 6 to 12 and Table 2.

TABLE 2

| Classification | ng/ml | Mean (μm) | Sd |
|---|---|---|---|
| Ctrl | — | 833.5567 | 58.78009 |
| WT | 0.01 | 1237.543 | 64.14704 |
| | 1 | 1286.943 | 59.92032 |
| | 100 | 1304.363 | 76.3394 |
| M3 mutant | 0.01 | 1739.657 | 122.5517 |
| | 1 | 1759.083 | 120.1073 |
| | 100 | 1809.76 | 141.1934 |
| M4 mutant | 0.01 | 1444.973 | 70.61137 |
| | 1 | 1573.837 | 27.24489 |
| | 100 | 1550.97 | 46.41372 |
| M5 mutant | 0.01 | 1365.46 | 48.78922 |
| | 1 | 1483.112 | 130.69 |
| | 100 | 1483.837 | 82.66543 |
| M6 mutant | 0.01 | 1455.1 | 52.42397 |
| | 1 | 1531.107 | 72.92847 |
| | 100 | 1418.417 | 88.17606 |

As can be confirmed from FIGS. 6 to 12 and Table 2, the differentiation-induced C2C12 cell lines treated with the ADAMTS1 wild type or mutants were differentiated into thicker and longer myotubes compared with the differentiation-induced C2C12 cell line treated with the differentiation medium.

In addition, the myotube length was longer in the cell lines treated with the ADAMTS1 mutants than the wild type, and especially, the longest myotubes were differentiation-induced by M3 mutant.

Example 6: Extent of Adipogenesis

Adipose-derived mesenchymal stem cell line (ATCC, PCS-500-011) was cultured in a mesenchymal stem cell line exclusive medium (ATCC, PCS-500-030) comprising 2% fetal bovine serum, 5 ng/ml recombinant human epithelial cell factor, and 5 ng/ml recombinant human fibroblast growth factor, sold by ATCC. During cell differentiation, the medium was replaced with a medium in which StemPro medium (Gibco, A10410-01) was mixed with an additive (Gibco, A10065-01) provided by the manufacturer, and the differentiation into adipocytes was induced while the medium was replaced with new StemPro medium every 3 days for a total of 14 days. During the induction of differentiation, the cells were treated with ADAMTS1 wild type or M3 mutant recombinant protein at a concentration of 1 ng/ml or 100 ng/ml once daily.

In order to examine the extent of adipogenesis from the differentiation-induced adipose-derived mesenchymal stem cells, Oil Red O staining was used. Specifically, the differentiated cells were fixed in 10% formalin and stained with Oil Red O staining solution. The stained cells were observed under a microscope, and then the deposited dye was extracted using 100% isopropanol. The extracted dye was quantified by measurement of absorbance at a wavelength of 520 nm, and the results are shown in FIGS. 13 and 14 and Table 3.

TABLE 3

| Diff.− | Diff.+ | WT 1 (ng/ml) | WT 100 (ng/ml) | M3 1 (ng/ml) | M3 100 (ng/ml) |
|---|---|---|---|---|---|
| 0.120542 | 1 | 0.720773 | 0.731024 | 0.659033 | 0.67393 |
| 0.039364 | 0 | 0.032979 | 0.059734 | 0.086981 | 0.03776 |

As can be confirmed from FIGS. 13 and 14 and Table 3, both the wild type and M3 mutant of ADAMTS1 inhibited the differentiation of adipose-derived mesenchymal stem cells into adipocytes.

Example 7: Intracellular Glucose Uptake

The intracellular glucose uptake that changes according to muscle differentiation increasing activity was measured using 2-(N-(7-nitrobenz-2-oxa-1,3-diazol-4-yl)amino-2-de-oxyglucose (2-NBDG), a fluorescent glucose analogue. During the induction of differentiation for 8 days, C2C12 cell line was treated with ADAMTS1 or M3 mutant recombinant protein once daily at a concentration of 100 ng/ml, respectively. The differentiation-induced cells were treated with glucose-free DMEM for 2 hours, and thereafter, treated with 100 nM insulin for 15 minutes, and then 2-NBDG was added thereto to a final concentration of 100 μg/ml. The glucose uptake was measured at 485 nm for excitation and 535 nm for emission, and the results are shown in FIG. 15 and Table 4.

TABLE 4

| Classification | Ins− | | | Ins+ | | |
|---|---|---|---|---|---|---|
| | — | WT | M3 | — | WT | M3 |
| #1 | 1 | 1.297038 | 1.531155 | 1.246397 | 1.897571 | 2.269298 |
| #2 | 0.843478 | 1.31864 | 1.53383 | 1.508469 | 1.81309 | 2.228877 |
| #3 | 0.687519 | 1.33964 | 1.507814 | 1.60218 | 1.956826 | 2.177554 |
| #4 | 0.851029 | 0.92594 | 1.538645 | 1.544263 | 1.895672 | 2.009495 |
| Mean | 0.845506 | 1.220315 | 1.527861 | 1.475328 | 1.89079 | 2.171306 |
| SD | 0.127623 | 0.197019 | 0.013719 | 0.157428 | 0.05907 | 0.11422 |

As can be confirmed from FIG. 15 and Table 4, the extent of glucose uptake of the differentiation-induced C2C12 cell line increased under insulin treatment, and especially, the C2C12 cell line, for which the differentiation into myocytes was induced by the treatment with M3 mutant ADAMTS1, showed more increased glucose uptake compared with the cell line for which the differentiation was induced by the treatment with the wild type.

Example 8: Weight Recovery in Muscle Loss Animal Model

12-Week-old C57BL/6 mice were administered with dex-amethasone through intraperitoneal injection at a concentration of 50 mg/kg daily for 12 days. Simultaneously, the mice were administered through intraperitoneal injection with 100 μl of M3 mutant ADAMTS1 at concentrations of 0.02 μg/μl (Low), 0.2 μg/μl (Mid), and 2 μg/μl (High). The animal model was observed for weight recovery during administration for a total of 12 days.

As can be confirmed from FIG. 16, the animal model with muscle loss induced by dexamethasone administration showed a distinctive weight loss compared with the normal group, and when the animal model was treated with M3 mutant ADAMTS1, all the Low, Mid, and High dose groups showed significant weight recovery. Especially, the weight recovery observed in the high dose group exceeded the normal level.

Example 9: Weight Recovery of TA and GA Muscle Tissues in Muscle Loss Animal Model To examine weight changes of muscle tissues in a muscle atrophy animal model obtained by administration of 12-week-old C57BL/6 mice with dexamethasone for 12 days, an autopsy was performed, after the completion of administration, to extract TA and GA muscle tissues. The extracted muscle tissues were weighed and compared.

As can be confirmed from FIG. 17, the animal model with muscle atrophy induced by dexamethasone administration showed distinctive tissue weight losses of both of TA and GA tissues compared with the normal group, and when the muscle loss animal model was treated with M3 mutant ADAMTS1, the Mid dose group showed significant weight recovery of TA muscle tissue and the High dose group showed significant weight recovery of TA and GA muscle tissues.

Example 10: Recovery of Fat and Muscle in Muscle Loss Animal Model

12-Week-old C57BL/6 mice were administered with dex-amethasone through intraperitoneal injection at a concentration of 50 mg/kg daily for 12 days, and simultaneously, the mice were administered through intraperitoneal injection with 100 μl of M3 mutant ADAMTS1 at a concentration of 2 μg/μl. After the completion of administration, the mice were anesthetized through inhalational anesthesia and then analyzed for muscle mass and body fat mass by using a Dual-energy X-ray Absorptiometry (DXA) device.

As can be confirmed from FIG. 18, both fat and muscle were significantly reduced in the animal model with muscle loss induced by dexamethasone administration. When the animal model with induced muscle atrophy was treated with M3 mutant ADAMTS1, both fat and muscle were recovered to the normal level.

Example 11: Increases in Expression of Muscle Differentiation-Related Genes in Muscle Loss Animal Model 12-Week-old C57BL/6 mice were administered with dex-amethasone through intraperitoneal injection at a concentration of 50 mg/kg daily for 12 days, and simultaneously, the mice were administered through intraperitoneal injection with 100 μl of M3 mutant ADAMTS1 at concentrations of 0.02 μg/μl (Low), 0.2 μg/μl (Mid), and 2 μg/μl (High). After the completion of administration of dexamethasone and M3 mutant ADAMTS1, an autopsy was performed to extract GA muscle tissue. The GA muscle tissue in a frozen state was homogenized using a pestle, and then RNA was extracted (Qiagen, 74104). The extracted RNA was prepared into cDNA using a cDNA synthesis reagent (Promega, A5000). The relative mRNA expression levels of MyoD, MyoG, Pax7, and MRF4, genes related to muscle differentiation, were compared from the synthesized cDNA by using a real-time polymerase chain reaction system (Applied Biosystems, Quantstudio3).

As can be confirmed from FIG. 19, when the animal model with muscle atrophy induced by dexamethasone treatment was treated with M3 mutant ADAMTS1, both the Low and High dose groups showed a significant increase in MyoD gene expression compared with the normal group and the dexamethasone treatment group.

Compared with the normal group, the dexamethasone treatment group showed significant decreases in MyoG, Pax7, and MRF4 expression levels, but the M3 mutant ADAMTS1 treatment showed significant increases in MyoG, Pax7, and MRF4 expression levels. This indicates that M3 mutant ADAMTS1 increased muscle differentiation by increasing the expression of muscle differentiation-related genes.

Example 12: Reductions in Expression of Muscle Differentiation Inhibition-Related Genes in Muscle Loss Animal Model 12-Week-old C57BL/6 mice were administered with dexamethasone through intraperitoneal injection at a concentration of 50 mg/kg daily for 12 days, and simultaneously, the mice were administered through intraperitoneal injection with 100 μl of M3 mutant ADAMTS1 at concentrations of 0.02 μg/μl (Low), 0.2 μg/μl (Mid), and 2 μg/μl (High). After the completion of administration of dexamethasone and M3 mutant ADAMTS1, an autopsy was performed to extract GA muscle tissue. The GA muscle tissue in a frozen state was homogenized using a pestle, and then RNA was extracted (Qiagen, 74104). The extracted RNA was prepared into cDNA using a cDNA synthesis reagent (Promega, A5000). The relative mRNA expression levels of MuRF1, Atrogin1, and Hes1, which are muscle differentiation inhibition-related genes, were compared from the synthesized cDNA by using a real-time polymerase chain reaction system (Applied Biosystems, Quantstudio3).

As can be confirmed from FIG. 20, when the animal model with muscle atrophy induced by dexamethasone treatment was treated with M3 mutant ADAMTS1, both the Low and High dose groups showed significant reductions in MuRF1, Atrogin1, and Hes1 gene expression. This indicates that M3 mutant ADAMTS1 can increase muscle differentiation by inhibiting muscle differentiation inhibition-related genes.

Example 13: Increase in Muscle Differentiation in Cells with Muscle Differentiation Inhibition Induced by Anticancer Drug (Cancer Cachexia Model)

While the C2C12 myoblast cell line was differentiation-induced in 24-well cell culture plates for 8 days, the cells were treated with the cisplatin anticancer drug at a concentration of 50 μM together with M3 ADAMTS1 mutant recombinant protein at concentrations of 0.1, 1, and 10 ng/ml, respectively. The differentiation-induced cells were fixed in methanol for 10 minutes. The plates were sufficiently washed with PBS three times, and then stained for 10 minutes with a mixture of 2.5 mg/ml of Jenner staining reagent dissolved in methanol and distilled water at 1:1. The stained plates were washed with distilled water and then dried, followed by observation under a microscope.

As can be confirmed from FIG. 21, when the cancer cachexia cell model with muscle differentiation inhibited by cisplatin treatment was treated with M3 mutant ADAMTS1, the shortened myotube length was significantly increased in a dose-dependent manner.

Example 14: Increase in Activity of Primary Muscle Cells

Primary myocytes were cultured in 96-well plates for 24 hours, and then the medium was replaced with a serum-free medium, followed by further culturing for 24 hours. Thereafter, the cells were treated with 10 μM BrdU and M3 ADAMTS1 mutant protein at concentrations of 0.01, 0.1, 1, 10, and 100 ng/ml, followed by culturing for 24 hours. Then, the absorbance was measured at 450 nm by using a BrdU fluorescence measurement ELISA kit (Cell signaling technology, 6813S). An increase in the amount of newly synthesized DNA within the myocytes led to an increase in the measured absorbance, indicating an increase in activity of muscle cells.

As can be confirmed from FIG. 22, the treatment with M3 mutant ADAMTS1 increased the activity of primary myocytes in a dose-dependent manner.

Although the present disclosure has been described in detail with reference to the specific features, it will be apparent to those skilled in the art that this description is only for a preferred embodiment and does not limit the scope of the present disclosure.

This application contains references to amino acid sequences and/or nucleic acid sequences which have been submitted concurrently herewith as the sequence listing text file entitled "000343usnp_SequenceListing.TXT", file size 17.1 kilobytes (KB), created on 14 Jun. 2023. The aforementioned sequence listing is hereby incorporated by reference in its entirety pursuant to 37 C.F.R. § 1.52 (e) (5).

---

What is claimed is:

1. An M3 mutant peptide of a disintegrin and metallo-protease with thrombospondin motifs 1 (ADAMTS1), the peptide consisting of the amino acid sequence of SEQ ID NO: 1 with deletions of amino acids at positions 222 to 251.

2. The M3 mutant peptide of claim 1, wherein the M3 mutant peptide further has deletions of amino acids at positions 413 to 967 of the peptide.

3. The M3 mutant peptide of claim 2, wherein the M3 mutant peptide consists of the amino acid sequence of SEQ ID NO: 2.

4. A method for treating a muscle disease, obesity, or diabetes, comprising:
   administering to a subject in need thereof a composition comprising a therapeutically effective amount of the peptide of claim 1.

5. The method of claim 4, wherein the muscle disease is selected from the group consisting of sarcopenia, amyotrophy, cancer cachexia, muscle injury, muscular dystrophy, atrophy of heart, atony, muscular dystrophy, muscular degeneration, and myasthenia.

* * * * *